United States Patent
Brinzari et al.

(10) Patent No.: US 11,395,793 B2
(45) Date of Patent: Jul. 26, 2022

(54) ZINC—AMINO ACID—LAURYL SULFATE COMPLEX WITH ANTIMICROBIAL ACTIVITY

(71) Applicant: Colgate-Palmolive Company, New York, NY (US)

(72) Inventors: Tatiana Brinzari, Piscataway, NJ (US); Michael Stranick, Bridgewater, NJ (US); Chi-Yuan Cheng, Hillsborough, NJ (US); Zhigang Hao, Bridgewater, NJ (US); Iraklis Pappas, Pennsauken, NJ (US); Greggory Marron, New Brunswick, NJ (US); Viktor Dubovoy, Cresskill, NJ (US); Long Pan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 184 days.

(21) Appl. No.: 16/599,163

(22) Filed: Oct. 11, 2019

(65) Prior Publication Data

US 2020/0129399 A1    Apr. 30, 2020

Related U.S. Application Data

(60) Provisional application No. 62/749,714, filed on Oct. 24, 2018.

(51) Int. Cl.
| | | |
|---|---|---|
| *A61K 8/44* | (2006.01) |
| *A61K 8/02* | (2006.01) |
| *A61K 8/27* | (2006.01) |
| *A61K 8/46* | (2006.01) |
| *A61Q 11/00* | (2006.01) |

(52) U.S. Cl.
CPC ............... *A61K 8/44* (2013.01); *A61K 8/022* (2013.01); *A61K 8/27* (2013.01); *A61K 8/463* (2013.01); *A61Q 11/00* (2013.01); *A61K 2800/58* (2013.01); *A61K 2800/92* (2013.01)

(58) Field of Classification Search
CPC .......... A61K 8/27; A61K 8/44; A61K 8/8176; A61K 8/24; A61K 8/21; A61Q 11/00
USPC .......................................................... 424/49
IPC ........................... A61K 8/21,8/24; A61Q 11/00
See application file for complete search history.

(56) References Cited

U.S. PATENT DOCUMENTS

| | | |
|---|---|---|
| 9,763,865 B2 | 9/2017 | Pan |
| 9,943,473 B2 | 4/2018 | Pan |
| 10,245,222 B2 | 4/2019 | Pan |
| 2019/0183766 A1 | 6/2019 | Pan |

FOREIGN PATENT DOCUMENTS

| | | |
|---|---|---|
| WO | 2014/098825 | 6/2014 |
| WO | 2015/195124 | 12/2015 |
| WO | 2017/000837 | 1/2017 |
| WO | 2017/100116 | 6/2017 |

OTHER PUBLICATIONS

International Search Report and the Written Opinion of the International Searching Authority issued in International Application PCT/US2019/055755 dated Jan. 24, 2020.

*Primary Examiner* — Walter E Webb

(57) ABSTRACT

Described herein are zinc-amino acid-lauryl sulfate complexes and oral care compositions comprising the same; and methods of making and using the same are also described.

16 Claims, 12 Drawing Sheets

ZINC—AMINO ACID—LAURYL SULFATE COMPLEX WITH ANTIMICROBIAL ACTIVITY

CROSS REFERENCE TO RELATED APPLICATIONS

This application claims the benefit of priority to U.S. Provisional Patent Application No. 62/749,714, filed on Oct. 24, 2018.

BACKGROUND

Zinc and basic amino acids are known to have several benefits and are currently used as active materials in oral care compositions. Zinc has been shown to have antibacterial properties in plaque and caries studies. Arginine and other basic amino acids have benefits in combating cavity formation and tooth sensitivity. Arginine was initially introduced as an additive to oral care compositions for the treatment of tooth sensitivity. When combined with calcium, arginine has been clinically proven to be effective in treating dentinal sensitivity by plugging and sealing dentinal tubules. Basic amino acids are also known to have significant anticaries benefits.

Zinc-amino acid complex forms a soluble cationic moiety, which in turn may form a salt with a halide or other anion. A zinc-lysine complex ("ZLC") having the chemical structure $[Zn(C_6H_{14}N_2O_2)_2Cl]^+Cl^-$ has been described in prior art (e.g., WO 2014/098813). When placed in an oral care formulation, this complex provides an effective concentration of zinc ions to the enamel, thereby protecting against erosion, reducing bacterial colonization and biofilm development, and providing enhanced shine to the teeth (WO 2014/098824). Moreover, upon use, the formulation provides a precipitate that can plug the dentinal tubules, thereby reducing the sensitivity of the teeth.

In oral care formulations containing zinc and amino acids, other ingredients present in the formulations can potentially interact with zinc and amino acids to form new species in the final product and affect their performance. The present invention relates to the identification of new complexes formed by the interaction of zinc-amino acid complexes and sodium lauryl sulfate.

BRIEF SUMMARY

The present invention describes zinc-amino acid-lauryl sulfate complexes. In some embodiments, the amino acid in the complex is a basic amino acid. In a preferred embodiment, the zinc-basic amino acid-lauryl sulfate complex is a zinc-arginine (Arg)-lauryl sulfate (LS) or zinc-lysine (Lys)-lauryl sulfate having the chemical structure $[Zn(Arg)_2](LS)_2$ or $[Zn(Lys)_2](LS)_2$. In an embodiment, the zinc-amino acid-lauryl sulfate complex is in powder form.

The present invention also provides methods of producing a zinc-basic amino acid-lauryl sulfate complex by combining sodium lauryl sulfate and a zinc-amino acid complex in an aqueous solution, e.g., an aqueous solution having pH of from 6 to 9, e.g., from 6.5-8.5, or from 7 to 8. In some embodiments, the method further comprises a step of filtering and drying the zinc-amino acid-lauryl sulfate complex.

The present invention also provides oral care compositions comprising a zinc-amino acid-lauryl sulfate complex, e.g., zinc-basic amino acid-lauryl sulfate complex, e.g., zinc-arginine-lauryl sulfate or zinc-lysine-lauryl sulfate. In some embodiments, the zinc-amino acid-lauryl sulfate complex is added to the composition as a preformed complex. In some embodiments, the zinc-amino acid-lauryl sulfate complex may be present in an amount of 0.1-10% by weight of the composition.

The present invention also provides use of a zinc-amino acid-lauryl sulfate complex in powder form for the manufacture of an oral care composition for reducing and inhibiting acid erosion of the enamel, cleaning the teeth, reducing bacterially-generated biofilm and plaque, reducing gingivitis, inhibiting tooth decay and formation of cavities, and reducing dentinal hypersensitivity.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The present invention will become more fully understood from the detailed description and the accompanying drawings.

DETAILED DESCRIPTION

Figure 1:
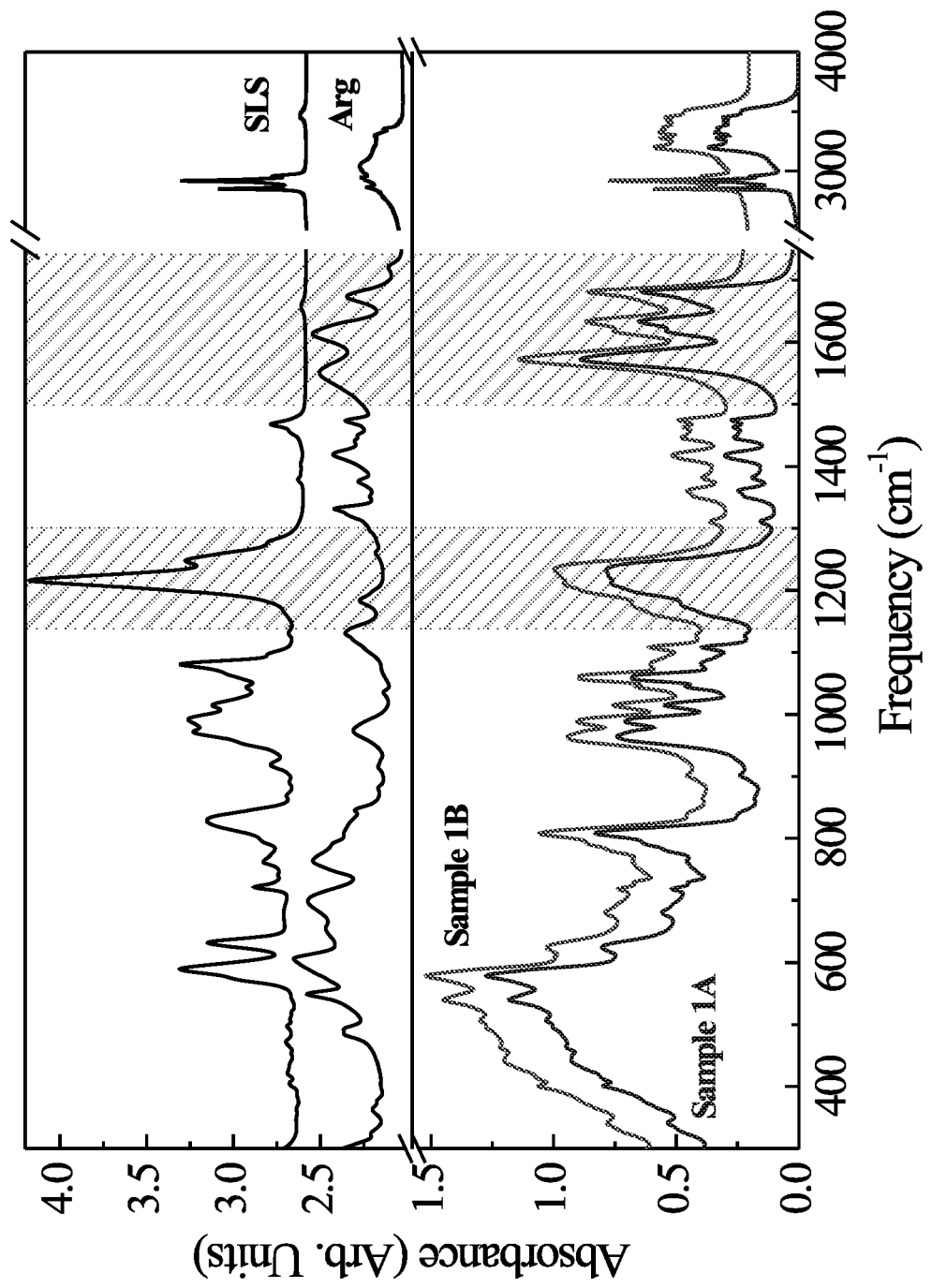
FIG. 1 shows the infrared spectra of sample 1A, sample 1B, L-arginine, and SLS powders. Shaded regions are examples of SLS and arginine corresponding bands that can be used for the identification of these components in sample 1A and 1B. Spectra are offset for clarity.

The following description of the preferred embodiment(s) is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

As used herein, the term "preformed complex" means that the zinc-amino acid-lauryl sulfate complex is not formed in situ in the oral care composition, e.g. through the reaction of zinc, amino acid and lauryl sulfate.

Unless otherwise specified, all percentages and amounts expressed herein and elsewhere in the specification should be understood to refer to percentages by weight. The amounts given are based on the active weight of the material.

The present invention relates to zinc-amino acid-lauryl sulfate complexes. Some commercialized oral care products contain zinc-amino acid complexes (e.g., ZLC) or contain both zinc ion sources (e.g., zinc oxide or zinc citrate) and amino acids (e.g., lysine or arginine). Zinc and amino acid can potentially interact with other ingredients present in the oral care products to form a new compound, thus affecting the stability of zinc, amino acid or zinc-amino acid complex in the product. The inventors have found that zinc-amino acid complexes (e.g., ZLC and zinc arginate) interact with sodium lauryl sulfate, a surfactant that also possesses antibacterial activity, to form water insoluble zinc-amino acid-lauryl sulfate complexes. In contrast to ZLC and zinc arginate $[Zn(Arg)_2]^{2+}$, the zinc-amino acid-lauryl sulfate complexes are insoluble in water. Thus, the zinc-amino acid-lauryl sulfate complexes of the present invention offer opportunities to provide slow release of three active materials (zinc, amino acid and lauryl sulfate), while avoiding the unpleasant metallic taste and aftertaste of soluble zinc compounds. The water-insoluble zinc-amino acid-lauryl sulfate complexes may also occlude dentin tubules. Thus, the zinc-amino acid-lauryl sulfate complexes can be used as a dentin tubule occlusion agent in oral care products. In addition, it has been found that the zinc-amino acid-lauryl sulfate complexes of the present invention have better antibacterial activity compared to corresponding zinc-amino acid complexes (e.g., ZLC and zinc arginate). Since the zinc-amino acid-lauryl sulfate complexes are insoluble upon preparation, they can be prepared as a dry powder for use in manufacturing oral care products comprising the zinc-amino acid-lauryl sulfate complexes. Use of the dried powder would allow savings on the quantities of starting materials and overall liquid contents that need to be added into a product to achieve a given final concentration.

The invention provides, in one aspect, zinc-amino acid-lauryl sulfate complexes. The terms "zinc-amino acid-lauryl sulfate complex" or "zinc-amino acid-lauryl sulfate" as used herein refers to a water insoluble complex comprising zinc, amino acid and lauryl sulfate. In this disclosure, lauryl sulfate is sometimes referred to as "LS". The zinc-amino acid-lauryl sulfate complexes are formed by combining a zinc-amino acid complex, e.g., ZLC or zinc arginate, and sodium lauryl sulfate (SLS) in an aqueous solution. Commercial SLS products are usually a mixture of sodium alkyl sulfates with carbon chains of various lengths, e.g., $C_{12}$-$C_{18}$, mainly lauryl. Therefore, the zinc-amino acid-lauryl sulfate complex of the invention may contain a mixture of alkyl sulfates with carbon chains of various lengths, e.g., $C_{12}$-$C_{18}$. The term "lauryl sulfate" or "LS" as used herein refers to an alkyl sulfate with $C_{12}$ carbon chain or a mixture of alkyl sulfates with carbon chains of various lengths, e.g., $C_{12}$-$C_{18}$ alkyl sulfates. In some embodiments, lauryl sulfate is a mixture of $C_{12}$-$C_{18}$ alkyl sulfates.

In some embodiments, the zinc-amino acid-lauryl sulfate complexes of the present invention have the chemical structure $[Zn(\text{amino acid})_2](LS)_2$. The theoretical molar ratio of Zn:amino acid:LS in the complex is 1:2:2. However, the zinc-amino acid-lauryl sulfate complex of the present invention may comprise a small amount, e.g., less than 10%, less than 5%, less than 2%, less than 1%, less than 0.5%, less than 0.1%, or less than 0.01%, of impurities such as SLS (sodium lauryl sulfate), ZnO and $Zn(OH)_2$.

In some embodiments, the zinc-amino acid-lauryl sulfate complexes of the present invention are in powder form.

Examples of amino acid in the zinc-amino acid-lauryl sulfate complex of the present invention include, but are not limited to, the common natural amino acids, e.g., lysine, arginine, histidine, glycine, serine, threonine, asparagine, glutamine, cysteine, selenocysteine, proline, alanine, valine, isoleucine, leucine, methionine, phenylalanine, tyrosine, tryptophan, aspartic acid, and glutamic acid. In preferred embodiments, the amino acid is a basic amino acid. The term "basic amino acid" as used herein refers to naturally occurring basic amino acids, such as arginine, lysine, and histidine, as well as any basic amino acid having a carboxyl group and an amino group in the molecule, which is water-soluble and provides an aqueous solution with a pH of about 7 or greater. Accordingly, basic amino acids include, but are not limited to, arginine, lysine, citrulline, ornithine, creatine, histidine, diaminobutanoic acid, diaminopropionic acid, salts thereof or combinations thereof. In some embodiments, the amino acid is lysine or arginine. In certain embodiments, the amino acid is lysine. In other embodiments, the amino acid is arginine.

The zinc-amino acid-lauryl sulfate complexes of the present invention may be prepared by a process comprising combining sodium lauryl sulfate and a zinc-amino acid complex in an aqueous solution. In some embodiments, pH of the solution in which sodium lauryl sulfate and a zinc-amino acid complex are combined is from 6 to 9, e.g. from 6.5-8.5 or from 7 to 8. In other embodiments, pH of the solution in which sodium lauryl sulfate and a zinc-amino acid complex are combined is not adjusted. In some embodiments, the prepared zinc-amino acid-lauryl sulfate complexes may be further filtered and dried to be a powder.

In some embodiments, the zinc-amino acid complex that is combined with sodium lauryl sulfate is $[Zn(Lys)_2Cl]^+Cl^-$ (ZLC) or ($[Zn(Arg)_2Cl]^+Cl$). These zinc-amino acid complexes can be prepared by combining ZnO, Lysine-HCl (or Arginine) and HCl in an aqueous solution, as described in WO 2014/098813. The formation of a white precipitate comprising zinc-amino acid-lauryl sulfate complexes occurs immediately upon combining sodium lauryl sulfate and the zinc-amino acid complex.

Alternatively, the zinc-amino acid complex that is combined with sodium lauryl sulfate-lauryl sulfate may be prepared by combining a zinc ion source and an amino acid in an aqueous solution. In some embodiments, the zinc ion source is a water soluble zinc ion source, e.g., zinc chloride. In some embodiments, the amino acid is a basic amino acid, e.g., arginine or lysine. In some embodiments, pH of the solution in which the zinc ion source and the amino acid are combined is from 6 to 9, e.g. from 6.5-8.5 or from 7 to 8. In other embodiments, pH of the solution in which sodium lauryl sulfate and a zinc-amino acid complex are combined is not adjusted. The formation of a white precipitate comprising zinc-amino acid-lauryl sulfate complexes occurs immediately upon adding sodium lauryl sulfate to the zinc-amino acid complex solution prepared by combining a zinc ion source and an amino acid in an aqueous solution.

The invention thus provides, in one aspect, zinc-amino acid-lauryl sulfate complexes (Compound 1).

In various aspects, Compound 1 included the following:
1.1 Compound 1, wherein the zinc-amino acid-lauryl sulfate has the chemical structure [Zn(amino acid)$_2$](LS)$_2$.
1.2 Compound 1 or 1.1, wherein the zinc-amino acid-lauryl sulfate is insoluble in an aqueous solution, e.g. in water at pH 7-8, e.g., wherein the zinc-amino acid-lauryl sulfate precipitates in an aqueous solution, e.g. in water at pH 7-8.
1.3 Any foregoing compound, wherein the zinc-amino acid-lauryl sulfate is a zinc-basic amino acid-lauryl sulfate.
1.4 Compound 1.3, wherein the amino acid is arginine or lysine.
1.5 Compound 1.4, wherein the amino acid is arginine.
1.6 Compound 1.5, wherein the zinc-amino acid-lauryl sulfate has the chemical structure [Zn(Arg)$_2$](LS)$_2$.
1.7 Compound 1.4, wherein the amino acid is lysine.
1.8 Compound 1.7, wherein the zinc-amino acid-lauryl sulfate has the chemical structure [Zn(Lys)$_2$](LS)$_2$.
1.9 Any foregoing compound, wherein the zinc-amino acid-lauryl sulfate is in powder form.
1.10 Any foregoing compound, wherein the zinc-amino acid-lauryl sulfate is prepared by a process comprising combining sodium lauryl sulfate and a zinc-amino acid complex in an aqueous solution.
1.11 Compound 1.10, wherein the zinc-amino acid complex is a zinc-basic amino acid complex, e.g., [Zn(Lys)$_2$Cl]$^+$Cl$^-$ (ZLC) or [Zn(Arg)$_2$Cl]$^+$Cl$^-$.
1.12 Compound 1.10, wherein the zinc-amino acid complex is prepared by combining a zinc ion source and an amino acid in an aqueous solution.
1.13 Compound 1.12, wherein the amino acid is a basic amino acid, e.g., arginine or lysine.
1.14 Compound 1.12 or 13, wherein the zinc ion source is a water soluble zinc salt, e.g., zinc chloride.
1.15 Any foregoing compound, wherein the lauryl sulfate is a mixture of C$_{12}$-C$_{18}$ alkyl sulfates.

The invention provides, in another aspect, methods (Method 2) for the production of zinc-amino acid-lauryl sulfate complexes (any of Compounds 1, et. seq.), comprising combining sodium lauryl sulfate and a zinc-amino acid complex in an aqueous solution, e.g. water.

In various aspects, Compound 1 included the following:
2.1 Method 2, wherein pH of the solution in which sodium lauryl sulfate and the zinc-amino acid complex is combined is from 6 to 9, e.g. from 6.5 to 8.5 or from 7 to 8.
2.2 Method 2, wherein pH of the solution in which sodium lauryl sulfate and the zinc-amino acid complex is not adjusted.
2.3 Any foregoing method, wherein the zinc-amino acid-lauryl sulfate is a zinc-basic amino acid-lauryl sulfate.
2.4 Method 2.3, wherein the zinc-amino acid complex is [Zn(Lys)$_2$Cl]$^+$Cl$^-$ (ZLC) or [Zn(Arg)$_2$Cl]$^+$Cl$^-$.
2.5 Method 2.3, wherein the zinc-amino acid complex is prepared by combining a soluble zinc salt, e.g., zinc chloride, and a basic amino acid, e.g., arginine or lysine, in an aqueous solution, e.g. water.
2.6 Method 2.5, wherein pH of the solution in which the sodium zinc salt and the basic amino acid is combined is from 6 to 9, e.g., from 6.5 to 8.5 or from 7 to 8.
2.7 Method 2.5, wherein pH of the solution in which the sodium zinc salt and the basic amino acid is not adjusted.
2.8 Any foregoing method, wherein the method further comprises a step of filtering and drying the zinc-amino acid-lauryl sulfate complex.
2.9 Any foregoing method, wherein the sodium lauryl sulfate is a mixture of sodium C$_{12}$-C$_{18}$ alkyl sulfates.

The invention provides, in another aspect, oral care compositions (Composition 3) comprising zinc-amino acid-lauryl sulfate complexes (any of Compounds 1, et. seq.), wherein the zinc-amino acid-lauryl sulfate complex is added to the composition as a preformed complex.

In various aspects, Composition 3 includes:
3.1. Composition 3, wherein the zinc-amino acid-lauryl sulfate is present in an amount of from 0.1 to 10%, from 0.5 to 10%, from 1 to 10%, from 2 to 10%, from 2 to 8%, from 2% to 4%, from 4% to 6%, from 6% to 8%, from 8% to 10%, or from 5% to 6% by weight of the composition.
3.2. Composition 3 or 3.1, wherein the oral care composition is a dentifrice.
3.3. Any foregoing composition, wherein the zinc-amino acid-lauryl sulfate is added to the composition in powder form.
3.4. Any foregoing composition, wherein the pH of the composition is 4.5-10.5, e.g., 6-9, 6.5-8.5, 7.0-8.5, 7.0-8.0, 7.5-8.0, or 8.0-8.5.
3.5. Any foregoing composition, wherein the composition comprises one or more soluble phosphate salts, e.g. selected from tetrasodium pyrophosphate (TSPP), sodium tripolyphosphate (STPP) and combinations thereof.
3.6. Any foregoing composition, wherein the composition comprises an effective amount of a fluoride ion source, e.g., providing 500 to 3000 ppm fluoride.
3.7. Composition 3.6, wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.
3.8. Any foregoing composition, wherein the composition comprises a humectant, e.g., selected from glycerin, sorbitol, propylene glycol, polyethylene glycol, xylitol, and mixtures thereof, e.g., comprising at least 30%, e.g., 30-50% glycerin, by weight of the composition.
3.9. Any foregoing composition, wherein composition further comprises one or more surfactants, e.g., selected from anionic, cationic, zwitterionic, and nonionic surfactants, and mixtures thereof, e.g., in an amount of from 0.01% to 5%, from 0.01% to 2%, from 1% to 2%, or about 1.5%, by weight of the composition.
3.10. Any foregoing composition, wherein the composition further comprises an anionic surfactant, e.g., a surfactant selected from sodium lauryl sulfate, sodium ether lauryl sulfate, and mixtures thereof, e.g., in an amount of from about 0.3% to about 4.5% by weight, 1-2%, or about 1.5% by weight of the composition.
3.11. Any foregoing composition, wherein the composition comprises a zwitterionic surfactant, for example a betaine surfactant, for example cocamidopropylbetaine, e.g. in an amount of 0.1%-4.5% by weight, e.g., 0.5-2% cocamidopropylbetaine by weight of the composition 3.12. Any foregoing composition, wherein the composition comprises gum strips or fragments.
3.13. Any foregoing composition, wherein the composition comprises flavoring, fragrance and/or coloring.
3.14. Any foregoing composition, wherein the composition comprises an effective amount of one or more antibacterial agents in addition to the zinc-amino acid-lauryl sulfate complex, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, honokiol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride.
3.15. Any foregoing composition, wherein the composition comprises an abrasive.
3.16. Composition 3.15, wherein the abrasive is selected from silica abrasives, calcium phosphate abrasives, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, and combinations thereof.
3.17. Any foregoing composition, wherein the composition comprises a whitening agent, e.g., a selected from the group consisting of peroxides, metal chlorites, perborates, percarbonates, peroxyacids, hypochlorites, and combinations thereof.
3.18. Any foregoing composition, wherein the composition comprises hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);
3.19. Any foregoing composition, wherein the composition comprises an agent that interferes with or prevents bacterial attachment, e.g., solbrol or chitosan.
3.20. Any foregoing composition, wherein the composition comprises a soluble calcium salt, e.g., selected from calcium sulfate, calcium chloride, calcium nitrate, calcium acetate, calcium lactate, and combinations thereof.
3.21. Any foregoing composition, wherein the composition comprises a physiologically or orally acceptable potassium salt, e.g., potassium nitrate or potassium chloride, in an amount effective to reduce dentinal sensitivity.
3.22. Any foregoing composition, wherein the composition comprises a breath freshener, fragrance or flavoring.
3.23. Any foregoing composition for use to reduce and inhibit acid erosion of the enamel, clean the teeth, reduce bacterially-generated biofilm and plaque, reduce gingivitis, inhibit tooth decay and formation of cavities, and reduce dentinal hypersensitivity.

The oral care composition used in the present invention can be in the form of any oral care formulations, including dentifrice, toothpaste, gel, mouthwash, powder, cream, strip, gum, bead, film, floss or any other known in the art. In some embodiments, the oral care composition used in the present invention is a dentifrice.

The oral care compositions of the invention contain an orally acceptable carrier. As used herein, an "orally acceptable carrier" refers to a material or combination of materials that are safe for use in the compositions of the invention, commensurate with a reasonable benefit/risk ratio. Such materials include but are not limited to, for example, water, humectants, ionic active ingredients, buffering agents, anti-calculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof. Such materials are well known in the art and are readily chosen by one skilled in the art based on the physical and aesthetic properties desired for the compositions being prepared.

The oral care composition of the present invention may further comprise a basic amino acid, e.g., arginine, in addition to the basic amino acid present in zinc-amino acid-lauryl sulfate complexes. The basic amino acids which can be used in the compositions include not only naturally occurring basic amino acids, such as arginine, lysine, and histidine, but also any basic amino acids having a carboxyl group and an amino group in the molecule, which are water-soluble and provide an aqueous solution with a pH of about 7 or greater. Accordingly, basic amino acids include, but are not limited to, arginine, lysine, citrullene, ornithine, creatine, histidine, diaminobutanoic acid, diamrinopropionic acid, salts thereof or combinations thereof. In a particular embodiment, the basic amino acids are selected from arginine, lysine, citrullene, and ornithine. In some embodiments, the basic amino acid is arginine, for example, L-arginine, or a salt thereof.

The oral care composition of the present invention may comprise dentin tubule occlusion agents. Such dentin tubule occlusion agents include, but are not limited to, arginine-calcium carbonate complexes, silicas, polymethyl vinyl ether-maleic acid (PMV/MA) copolymers, oxalate salts, strontium salts, and combinations thereof.

The oral care composition of the present invention may include desensitizing agents. Such desensitizing agents include, but are not limited to, potassium salts such as potassium nitrate, potassium bicarbonate, potassium chloride, potassium citrate, potassium tartrate, and potassium oxalate, capsaicin, eugenol, strontium salts, zinc salts, chloride salts, and combinations thereof. Such agents may be added in effective amounts, which preferably vary between about 0.01% to about 10% by weight based on the total weight of the composition, depending on the agent chosen. In some embodiments, the desensitizing agent is a potassium salt in an amount of at least about 5% by weight of a potassium salt based on the total weight of the composition, e.g., from about 5% to about 10% by weight of a potassium salt based on the total weight of the composition. In some embodiments, the desensitizing agent is potassium nitrate.

The oral care composition of the present invention may include one or more fluoride ion sources, e.g., soluble fluoride salts. A wide variety of fluoride ion-yielding materials can be employed as sources of soluble fluoride in the present compositions. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments, the fluoride ion source includes stannous fluoride, sodium fluoride, sodium monofluorophosphate as well as mixtures thereof. In certain embodiments, the oral care composition described herein may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions described herein at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counter ion in the salt.

The oral care compositions of the present invention may include other active ingredients. The active ingredients include, for example, zinc ion sources, anti-bacterial active agents, anti-tartar agents, anti-caries agents, anti-inflammatory agents, anti-sensitivity agents, basic amino acids, e.g., arginine, enzymes, nutrients, and the like. Actives useful herein are optionally present in the compositions of the present invention in safe and effective amounts that are sufficient to have the desired therapeutic or prophylactic effect in the human or lower animal subject to whom the active is administered, without undue adverse side effects (such as toxicity, irritation, or allergic response), commensurate with a reasonable risk/benefit ratio when used in the manner of this invention. The specific safe and effective amount of the active will vary with such factors as the particular condition being treated, the physical condition of the subject, the nature of concurrent therapy (if any), the specific active used, the specific dosage form, the carrier employed, and the desired dosage regimen.

One or more abrasive or polishing materials may also be included in the oral care composition of the present invention. The abrasive or polishing material can be any material that is acceptable for use in a dentifrice, does not excessively abrade dentin and is compatible with the other components of the oral care composition. Exemplary abrasive or polishing materials include, but are not limited to: silica abrasives, calcium phosphate abrasives, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, and combinations thereof.

The oral care composition of the present invention may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the composition. Polyoxyethylene is also commonly known as polyethylene glycol ("PEG") or polyethylene oxide. The polyoxyethylenes suitable for this composition will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions. Where present, the amount of foaming agent in the oral care composition (i.e., a single dose) is about 0.01 to about 0.9% by weight, about 0.05 to about 0.5% by weight, and in another embodiment about 0.1 to about 0.2% by weight.

The oral care compositions of the present invention may further include at least one surfactant or solubilizer in addition to lauryl sulfate that may be released from zinc-amino acid-lauryl sulfate complexes of the invention. Suitable surfactants include neutral surfactants (such as polyoxyethylene hydrogenated castor oil or fatty acids of sugars), anionic surfactants (such as sodium lauryl sulfate), cationic surfactants (such as the ammonium cation surfactants) or zwitterionic surfactants. These surfactants or solubilizers may be present in amounts of typically from 0.01% to 5%; from 0.01% to 2%; or from 1% to 2%; or about 1.5%, by weight of the composition. These amounts do not include lauryl sulfate that may be released from zinc-amino acid-lauryl sulfate complexes of the invention. Thus, the actual amount of surfactants or solubilizers in the oral care composition may be higher.

The oral care compositions of the present invention may include one or more humectants. Humectants can reduce evaporation and also contribute towards preservation by lowering water activity, and can also impart desirable sweetness or flavor to compositions. Suitable humectants include edible polyhydric alcohols such as glycerin, sorbitol, xylitol, propylene glycol as well as other polyols and mixtures of these humectants. Other useful materials may also include orally acceptable alcohols, or polymers, e.g., such as polyvinylmethyl ether maleic acid copolymers, polysaccharides (e.g. cellulose derivatives, for example carboxymethyl cellulose, or polysaccharide gums, for example xanthan gum or carrageenan gum). In some embodiments, the humectant can be present in an amount of from 20% to 60%, for example from 30% to 50%, for example from 40% to 45%, by weight of the composition.

The oral care compositions of the present invention may include a preservative. Suitable preservatives include, but are not limited to, sodium benzoate, potassium sorbate, methylisothiazolinone, paraben preservatives, for example methyl p-hydroxybenzoate, propyl p-hydroxybenzoate, and mixtures thereof.

The oral care compositions of the present invention may include a sweetener such as, for example, saccharin, for example sodium saccharin, acesulfam, neotame, cyclamate or sucralose; natural high-intensity sweeteners such as thaumatin, stevioside or glycyrrhizin; or such as sorbitol, xylitol, maltitol or mannitol. One or more of such sweeteners may be present in an amount of from 0.005% to 5% by weight, for example 0.01% to 1%, for example 0.01% to 0.5%, by weight of the composition.

The oral care compositions of the present invention may include a flavoring agent. Suitable flavoring agents include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. The flavoring agent is typically incorporated in the oral composition at a concentration of 0.01 to 3% by weight.

The invention further provides methods to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying an effective amount of a composition of the invention, e.g., any of Composition 3, et seq. to the teeth.

For example, in various embodiments, the invention provides methods to (i) reduce hypersensitivity of the teeth, (ii) reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; (xv) reduce tartar build-up, and/or (xvi) promote systemic health, including cardiovascular health, e.g., by reducing potential for systemic infection via the oral tissues, comprising applying any of Compositions 3, et seq. as described above to the oral cavity of a person in need thereof, e.g., one or more times per day. The invention further provides Compositions 3, et seq. for use in any of these methods.

The present invention further provides use of zinc-basic amino acid-lauryl sulfate complexes (any of Compounds 1, et. seq.) in powder form for the manufacture of an oral care composition for reducing and inhibiting acid erosion of the enamel, cleaning the teeth, reducing bacterially-generated biofilm and plaque, reducing gingivitis, inhibiting tooth decay and formation of cavities, and reducing dentinal hypersensitivity.

EXAMPLES

Example 1—Preparation and Characterization of Zinc-Arginine-Lauryl Sulfate Complex Sample 1A: SLS powder was dissolved in 20 g of $H_2O$ followed by pH adjustment with HCl to pH≈7. Arginine and $ZnCl_2$ were dissolved together in approximately 47.9 g of $H_2O$ (Table 1) resulting in a clear solution. The pH of this mixture was adjusted with HCl to pH=7 followed by its addition to previously prepared SLS solution. A formation of white precipitate occurred immediately. The precipitate was filtered, washed with approximately 200 mL of deionized water and dried at room temperature.

Sample 1B: SLS powder was dissolved in 20 g of $H_2O$ followed by pH adjustment with HCl to pH=8. Arginine and $ZnCl_2$ were dissolved together in approximately 47.9 g of $H_2O$ (Table 1) resulting in a clear solution. The pH of this mixture was adjusted with HCl to pH=8 followed by its addition to previously prepared SLS solution. A formation of white precipitate occurred immediately. The precipitate was filtered, washed with approximately 200 mL of deionized water and dried at room temperature.

TABLE 1

Raw materials and their quantities used in preparation of samples 1A and 1B.

| Reagent | $H_2O$ (g) | L-Arginine (g) | $ZnCl_2$ Anhydrous (g) | SLS (g) |
|---|---|---|---|---|
| Sample 1A | 67.91 | 3.86 | 1.03 | 5.14 |
| Sample 1B | 67.93 | 3.86 | 1.07 | 5.14 |

In addition to Samples 1A and 1B, control solutions without $ZnCl_2$ and without arginine were also prepared. The ratios between ingredients were kept the same as shown in Table 1. Arginine-SLS solutions at pH=7 and 8 remained clear. No visual signs of precipitation were apparent confirming that zinc ion is needed for the precipitate formation to occur. The combination of $ZnCl_2$ and SLS resulted in white precipitate at pH>6 due to the Zn-LS interaction/precipitation and competing reaction of zinc hydroxide formation.

To characterize the composition of the precipitate formed upon combination of $ZnCl_2$, arginine and SLS, infrared spectroscopic analysis was performed. Infrared spectra were collected using a Bruker Vertex 70 FTIR spectrometer (Bruker Optics, Billerica, Mass.) equipped with a GladiATR diamond ATR accessory (Pike technologies, Madison, Wis.). The spectral range was 80-4000 $cm^{-1}$ and a resolution of 4 $cm^{-1}$ was used. All measurements were carried out at room temperature. Infrared spectra are shown in FIG. 1. The vibrational spectra of samples 1A and 1B were compared with the pure arginine and SLS absorption profiles. Clear fingerprints of arginine and SLS are apparent in the spectra of samples 1A and 1B. For example, the band near 1200 $cm^{-1}$ that corresponds to the $SO_2$ asymmetric vibration ($v_{as}(SO_2)$) is clearly observed in sample 1A and 1B (Viana et al. (2012), Adv. Phys. Chem., 2012, 1-14). Strong C—H stretching modes ($v_{as}(CH)$) near 2900 $cm^{-1}$ serve as another distinct indicator of the lauryl sulfate component. A cluster of bands near 1600 $cm^{-1}$ is a unique fingerprint of arginine that arises due to a combination of bending modes of amino group and stretching vibrations of carboxylate and guanidinium groups (Barth (2000), Prog. Biophys. Mol. Biol., 74, 141-173; Hernández et al. (2010), J. Phys. Chem. B 114 (2), 1077-1088). Presence of both components, arginine and LS in the solid phase confirms that the major component of the precipitate in samples 1A and 1B cannot be attributed to zinc hydroxide or zinc lauryl sulfate formation. Importantly, the bands of arginine and lauryl sulfate in samples 1A and 1B are substantially different in their intensity, shape/width profile and peak positions from those of pure arginine and SLS compounds. This indicates modifications to their local structure due to interaction, which cannot be achieved just from a physical mixture of compounds. FTIR spectra of samples 1A and 1B are practically identical, suggesting their similar local structure and no significant effect of pH on complex formation, at least within pH 7-8 range.

To establish the ratio between zinc, arginine and lauryl sulfate as well as to identify the presence of other potential ions in the samples, elemental analysis of Zn, N, S, Na, and Cl was performed following a standard protocol. The results of the analysis are shown in Table 2.

residual SLS is present in the solid. The detection of Na also indicates that a small amount of SLS is present. When the moles of residual SLS are subtracted from the data, the mole fractions for each sample match those for $Zn(Arg)_2(LS)_2$. Thus the XPS results indicate that both samples are composed of $Zn(Arg)_2(LS)_2$, with a minor amount of residual SLS present in the solid.

TABLE 3

XPS analysis of samples 1A and 1B.

| Sample | Atomic Percent | | | | | | |
|---|---|---|---|---|---|---|---|
| | C | O | N | Na | Zn | Cl | S |
| Sample 1A | 64.89 | 17.79 | 12.00 | 0.46 | 1.47 | 0.00 | 3.40 |
| | arg | LS | Zn | Na | arg/Zn | arg/LS | LS/Zn |
| For $Zn(Arg)_2(LS)_2$ | | | | | 2.0 | 1.0 | 2.0 |
| Sample 1A | 3.00 | 3.40 | 1.47 | 0.46 | 2.0 | 0.9 | 2.3 |
| minus SLS | 3.00 | 2.94 | 1.47 | 0.00 | 2.0 | 1.0 | 2.0 |

| Sample | Atomic Percent | | | | | | |
|---|---|---|---|---|---|---|---|
| | C | O | N | Na | Zn | Cl | S |
| Sample 1B | 64.50 | 17.75 | 12.37 | 0.40 | 1.55 | 0.00 | 3.45 |
| | arg | LS | Zn | Na | arg/Zn | arg/LS | LS/Zn |
| For $Zn(Arg)_2(LS)_2$ | | | | | 2.0 | 1.0 | 2.0 |
| Sample 1B | 3.09 | 3.45 | 1.55 | 0.40 | 2.0 | 0.9 | 2.2 |
| minus SLS | 3.09 | 3.05 | 1.55 | 0.00 | 2.0 | 1.0 | 2.0 |

TABLE 2

Summary of elemental analysis for samples 1A and 1B.

| | Zn (%) | N (%) | S (%) | Na (%) | Cl (%) | Molar Ratio | |
|---|---|---|---|---|---|---|---|
| | | | | | | Arg/Zn | LS/Zn |
| Sample 1A | 6.18 | 10.32 | 5.28 | 0.00 | — | 1.95 | 1.74 |
| Sample 1B | 6.21 | 10.38 | 6.15 | 0.00 | 0.00 | 1.95 | 2.02 |
| Calc* | 6.92 | 11.86 | 6.79 | — | — | 2 | 2 |

*Calculated values of Zn, N, and S for $Zn(Arg)_2(LS)_2$

Figure 2:
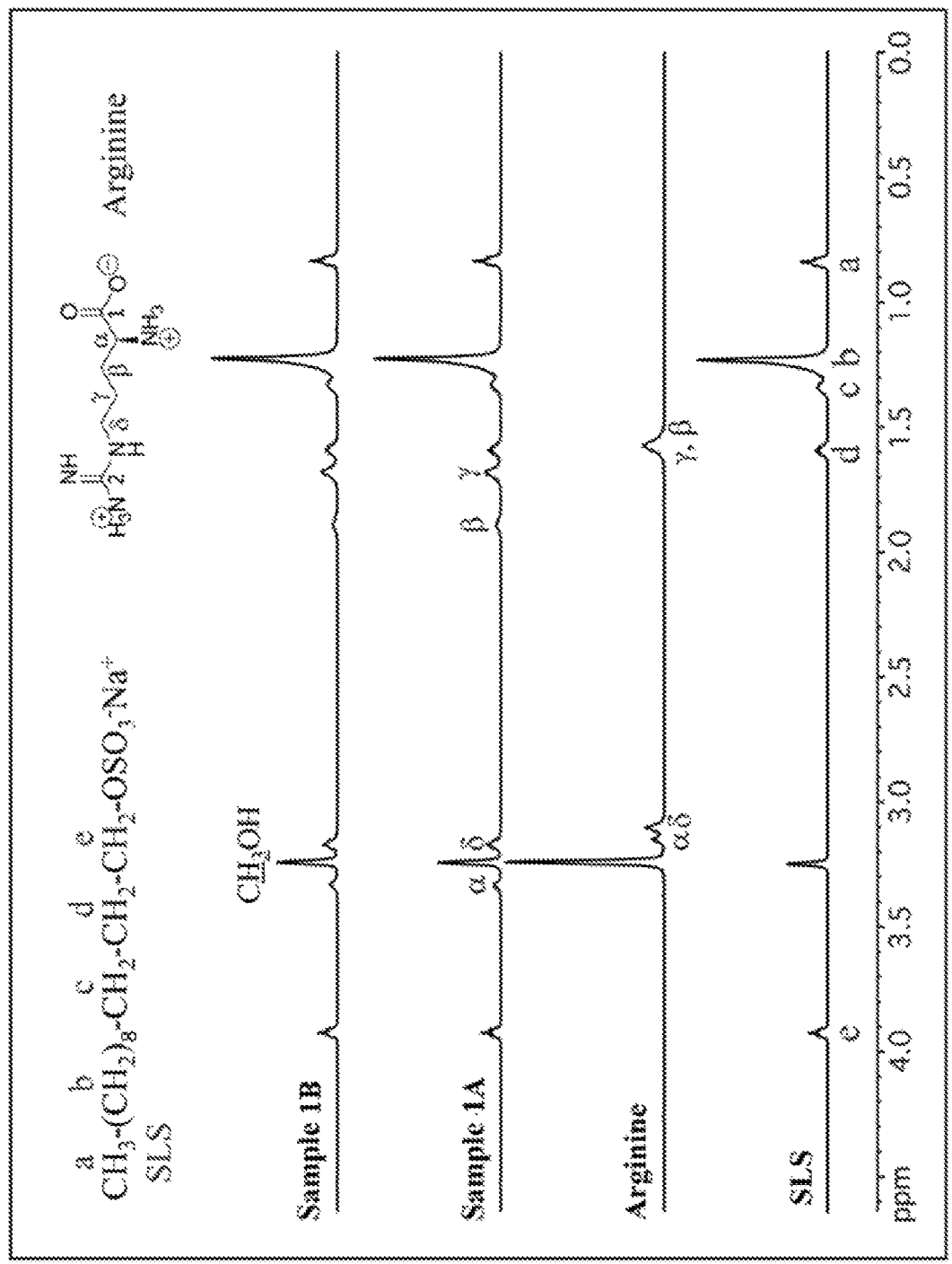
FIG. 2 shows $^1H$ NMR spectra of sample 1A, sample 1B, L-arginine, and SLS dissolved in deuterated methanol. The peaks are assigned to the corresponding $^1H$ of LS and arginine.

The experimental values in samples 1A and 1B are close to theoretical values for $Zn(Arg)_2(LS)_2$. The lower experimental values compared to theoretical/calculated values might be due to the presence of hydration/coordination water or residual moisture in the samples. These data suggest that the precipitate formed upon combination of $ZnCl_2$, arginine and SLS is $Zn(Arg)_2(LS)_2$. The composition of Samples 1A and 1B was further determined by X-Ray photoelectron spectroscopy (XPS) using a PHI VersaProbe II Scanning XPS Microprobe (Ulvac PHI, Chanhassen, Minn.). Duplicate analyses of each sample were conducted. Both samples were analyzed as powders using a 200 micron analysis area. The elemental composition in atomic percent for each sample as well as the mole percent and molar ratio for arginine, lauryl sulfate, Zn and Na are shown in Table 3. The elemental compositions of samples 1A and 1B are the same, indicating that pH has no significant effect on the compositions of the precipitated solids. The Arg/Zn mole ratios for samples 1A and 1B are consistent with that for $Zn(Arg)_2(LS)_2$. The Arg/LS and LS/Zn mole ratios for the samples differ from those of $Zn(Arg)_2(LS)_2$, indicating that To understand the structure of the $Zn(Arg)_2(LS)_2$ complex, $^1H$ NMR measurements were performed on 1 wt % samples in deuterated methanol solution. All NMR spectra were acquired on a Bruker Avance spectrometer (Bruker-Biospin, Billerica, Mass., USA) with a 5 mm BBI probe operating at 500.0 MHz for $^1H$ at 25° C. Diffusion coefficients of molecules were measured by $^1H$ pulsed-field gradient NMR spectroscopy using an observed broadband probe with a z axis gradient coil with maximal gradient strength of 72 G/cm. A double stimulated echo pulse sequence with bipolar gradient pulses and two spoil gradients were used. The diffusion time was 0.1 second. The duration of field gradient pulse was adjusted to be 4 milliseconds. The pulse gradients were incremented from 5 to 95% of the maximal gradient strength in a linear ramp with a total of experimental time of 30 minutes. FIG. 2 shows the $^1H$ NMR spectra of samples 1A and 1B as well as the spectra of pure L-arginine and SLS in methanol. The NMR spectra of samples 1A and 1B were identical. Proton chemical shifts of LS remained constant in samples 1A and 1B, whereas chemical shifts of α, β, γ and δ protons in arginine show significant changes in both samples compared to the pure compounds. This suggests that arginine coordinates to zinc in samples 1A and 1B, but LS does not. In addition, peak integrals of NMR spectra in samples 1A and 1B confirm that the stoichiometric ratio between arginine and LS is 1:1.

Figure 3:
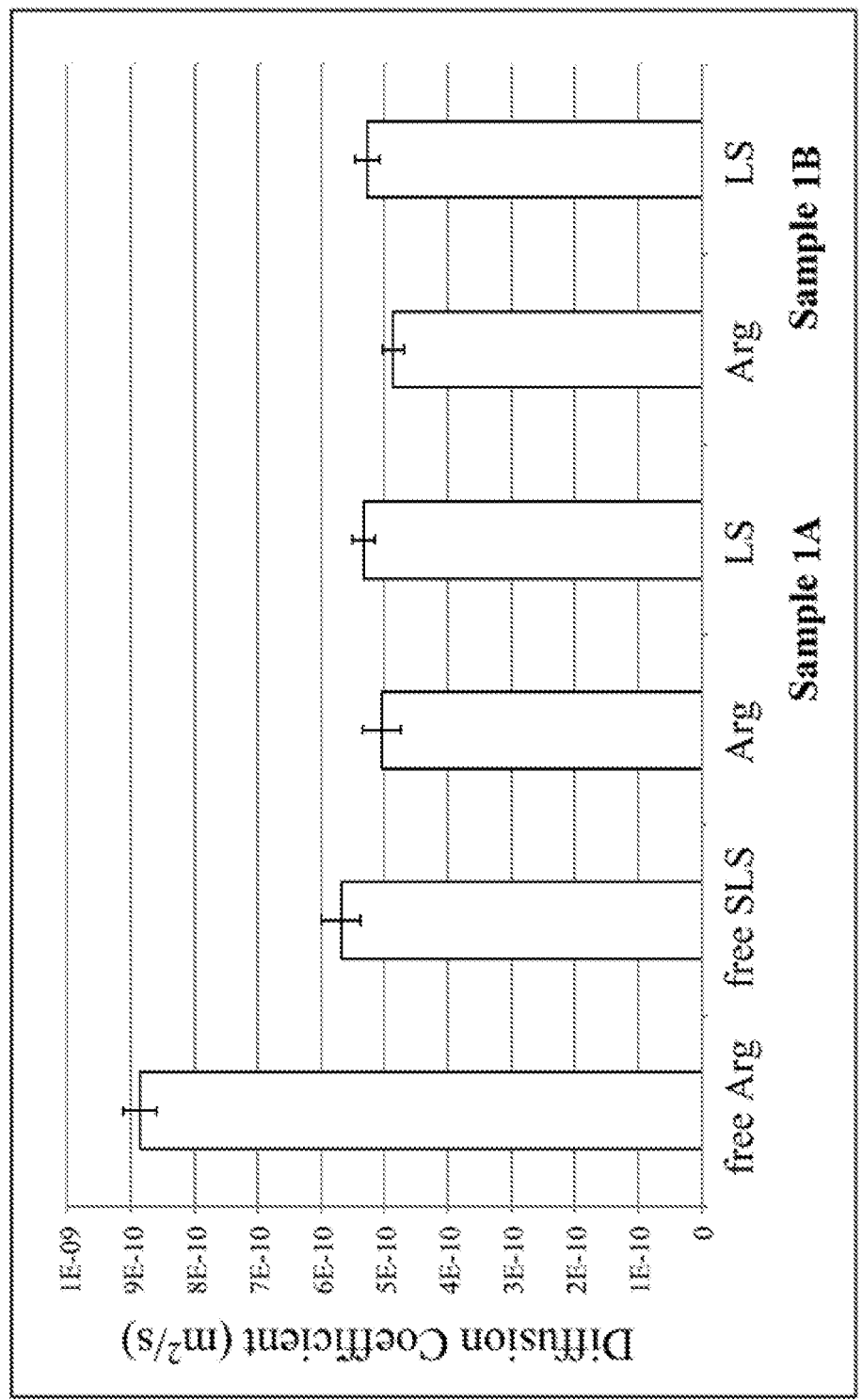
FIG. 3 shows diffusion coefficient of arginine and LS in samples 1A and 1B compared to that of pure arginine and SLS in methanol at 25° C.

To further confirm that arginine is bound to zinc in samples 1A and 1B, pulsed-field gradient NMR experiment was performed to measure the diffusion coefficient of arginine and LS in samples 1A and 1B in methanol. FIG. 3 show that diffusion coefficient of arginine in both samples is reduced by a factor of about 45% compared to that of pure arginine. In contrast, diffusion coefficients of LS free in solution and in samples 1A and 1B do not display significant changes. These results provide strong evidence that arginine is bound to zinc, and LS is a counterion of the zinc-arginine complex in methanol.

Figure 4A:
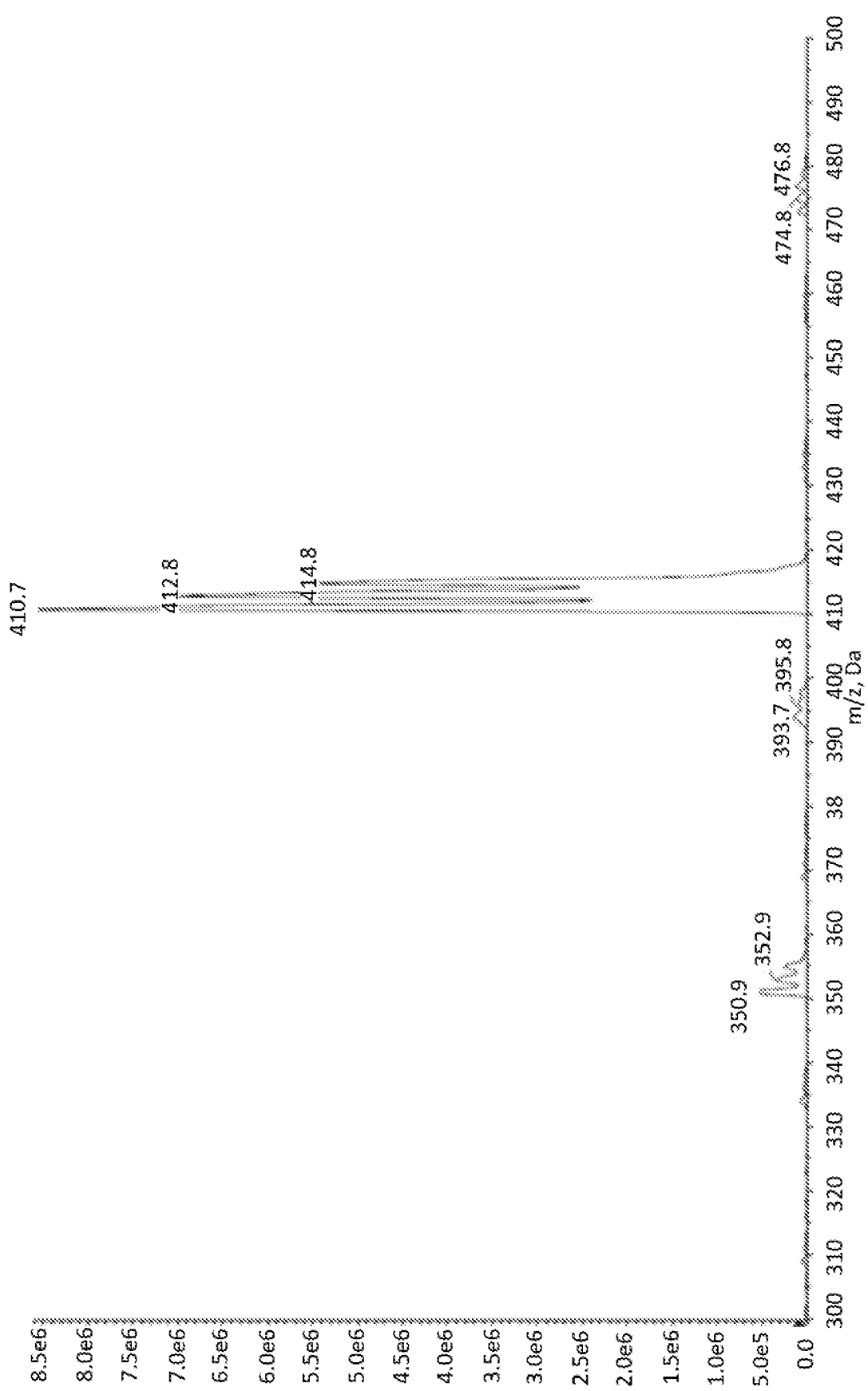
FIG. 4A shows the mass spectrum of sample 1A at 410.7/412.7/414.7 under a positive detection mode. The triplet peak is typical of zinc arginate.
Figure 4B:
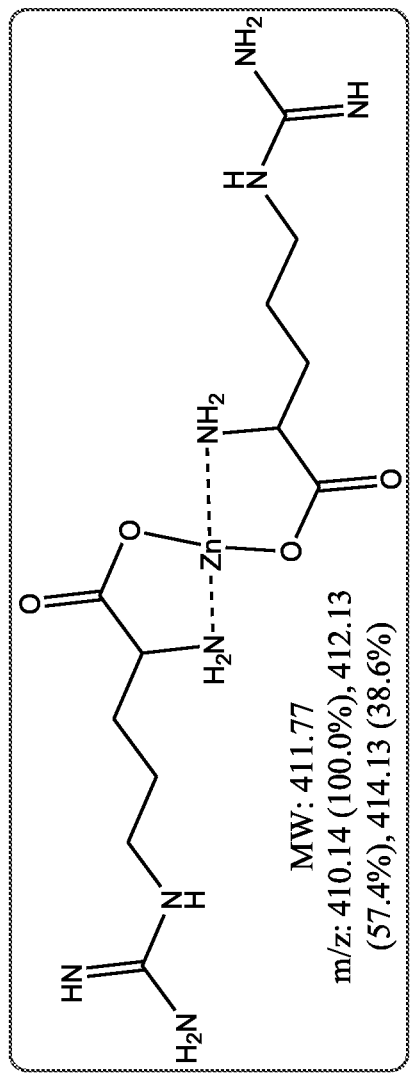
FIG. 4B shows the zinc arginate structure and the calculated m/z Dalton.
Figure 5:
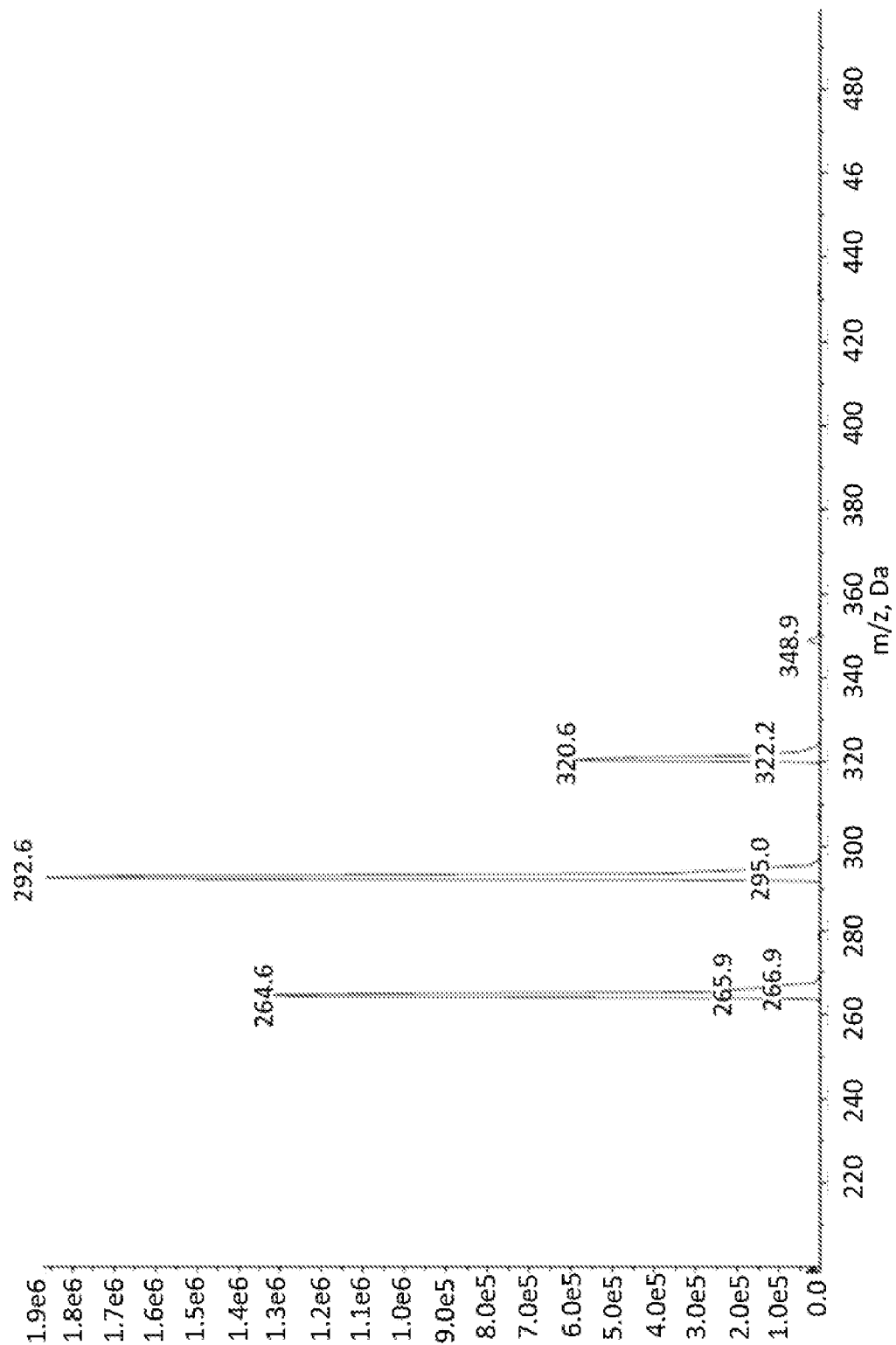
FIG. 5 shows the mass spectrum of sample 1A under a negative detection mode.

To confirm the $Zn(Arg)_2(LS)_2$ complex structure, LC-MS analysis was performed on sample 1B using a AB Sciex tandem mass spectrometer (AB Sciex LLC, Framingham, Mass., USA) equipped with an ESI interface and Agilent 1260 capillary LC system (Model Agilent 1260, Agilent Technologies, Palo Alto, Calif., USA). The capillary LC system was equipped with a capillary binary pump (Model G1376A), a DAD detector (G1315C), a micro vacuum degasser (Model G4225A), a thermostatted column compartment (Model G1316A). The capillary pump was set under the micro-flow mode. The sample was directly introduced into MS detector through a bypass injector. The flow rate was 70 μL/min and the injected volume was 5 μL. The AB Sciex tandem mass spectrometer was operated in the positive-ion mode under the following conditions. Nitrogen (>99.99%) was used for curtain gas at 10 psi, ion source gas 1 and 2 at 10 and 10 psi, respectively. ESI IonSpray voltage was set at 5.5 kV in ESI interface for positive mode and 4.5 kV for a negative mode. The declustering and entrance potential were set up at 80 and 5.5 v, respectively. The temperature of the ionization interface was maintained at 350° C. The total ion count (TIC) mode was used for sample analysis, and the MS screen range was from 50 to 1500 m/z. Data was acquired with an Analyst software 1.6.2 system (AB Sciex LLC, Framingham, Mass., USA). FIGS. 4A and B indicate that one zinc ion is coordinated with two arginine molecules and FIG. 5 shows the presence of free LS with chain distribution. The four peaks with the different mass unit of 28 Dalton indicate the LS distribution with $[(CH_2)_2]$ variation from $C_{12}$ to $C_{18}$. No Zn-Arg-LS complex was identified in either positive or negative mode on MS detector.

The presence of free LS in both NMR and MS data demonstrates that the $Zn(Arg)_2(LS)_2$ compound dissociates in methanol. This suggests that LS may act as a counterion to $[Zn(Arg)_2]^{2+}$ complex with the overall compound structure presented as $[Zn(Arg)_2](LS)_2$.

Geometry optimizations and harmonic frequency calculations were performed at the B3LYP/BS1 level in aqueous solution using the SMD solvation model, BS1 designating a mixed basis set of SDD for zinc and 6-31G(d,p) for other atoms. Because the M06 functional includes noncovalent interactions and gives refined energies for metal-organic complexes, single-point energies were calculated for all of the B3LYP/BS1-optimized structures at the M06/BS2 level with solvation effects modeled by SMD in aqueous solution, BS2 denoting a mixed basis set of SDD for zinc and 6-311++G(d,p) for other atoms. The B3LYP/BS1-calculated harmonic frequencies were used to obtain zero-point energy-corrected Gibbs free energies at 298.15 K and 1 atm. The Density Functional Theory (DFT) calculation is shown below.

(1) $\Delta G^0 = -53.2$ kcal/mol

The DFT result (ΔG: −53.2 kcal/mol) suggests that $[Zn(Arg)_2]^{2+}$ is a stable species existing in aqueous solution.

Example 2—Preparation and Characterization of Zinc-Lysine-Lauryl Sulfate Complex Three samples of zinc-lysine-lauryl sulfate complex were prepared in this study. Samples 2A and 2B were prepared from the ZLC pre-mix and SLS using the ratios of ZLC:SLS:$H_2O$ as shown in Table 3. Sample 2C was prepared from $ZnCl_2$+Lysine and SLS and was designed to mimic the preparation of $[Zn(Arg)_2](LS)_2$ complex described in Example 1. In addition to samples 2A, 2B and 2C, a control solution (sample 2D) without zinc was also prepared. The Lysine-SLS solution at pH=8 remained clear; no visual signs of precipitation were apparent confirming that the zinc ion is needed for the precipitate formation to occur.

TABLE 4

Raw materials and their quantities used in preparation of samples 2A, 2B, 2C, and 2D.

| Reagent (g) | Sample 2A | Sample 2B pH = 8 | Sample 2C pH = 8 | Sample 2D Control |
|---|---|---|---|---|
| ZnO | 2.10 | 2.10 | — | — |
| $ZnCl_2$ Anhydrous | — | — | 1.07 | — |
| L-Lysine-HCl | 9.44 | 9.44 | — | — |
| L-Lysine | — | — | 3.24 | 3.24 |
| HCl (conc.) (for ZLC pre-mix) | 1.37 | 1.36 | — | — |
| $H_2O$ (for SLS) | 15.02 | 15.00 | 20.01 | 20.09 |
| $H_2O$ (for Zn/Lys) | 14.99 | 16.51 | 47.89 | 47.84 |
| SLS | 3.49 | 3.60 | 5.14 | 5.15 |

Sample 2A (no pH adjustment): ZLC pre-mix was made by combining ZnO, L-Lysine-HCl, HCl (concentrated) and 15 g of $H_2O$ (Table 4). The mixture was stirred for one day to allow all of the ZnO to solubilize. SLS powder was dissolved in a separate container in 15 g of $H_2O$. Once the foam settled, the SLS solution was slowly added to the ZLC pre-mix under constant stirring. The formation of a white precipitate occurred immediately. The mixture was stirred for several hours and allowed to equilibrate for 1 day. The precipitate was filtered, washed with approximately 250 mL of deionized water and dried at room temperature.

Sample 2B (pH=8): ZLC pre-mix was made by combining ZnO, L-Lysine-HCl, HCl (concentrated) and 16.5 g of $H_2O$ (Table 4). The mixture was stirred for one day to allow all of the ZnO to solubilize. SLS powder was dissolved in a separate container in 15 g of $H_2O$ and foam was allowed to settle. Prior to combining ZLC and SLS, the pH of both solutions was adjusted to pH=8. The ZLC pre-mix solution was filtered through the 0.45 micron filter to remove zinc hydroxide partially formed at this pH. Upon combination of ZLC and SLS the formation of a white precipitate occurred immediately. The mixture was stirred for several hours and allowed to equilibrate for 1 day. The precipitate was filtered, washed with approximately 250 mL of deionized water and dried at room temperature.

Sample 2C (pH=8): SLS powder was dissolved in 20 g of $H_2O$ followed by pH adjustment with HCl to pH=8. Lysine and $ZnCl_2$ were dissolved together in approximately 48 g of $H_2O$ (Table 4) resulting in a clear solution. The pH of this mixture was adjusted with HCl to pH=8 followed by its addition to the previously prepared SLS solution. The formation of a white precipitate occurred immediately. The mixture was stirred for several hours and allowed to equilibrate for 1 day. The precipitate was filtered, washed with approximately 250 mL of deionized water and dried at room temperature.

Sample 2D (Control): SLS powder was dissolved in 20 g of $H_2O$ followed by pH adjustment with HCl to pH=8. Lysine was dissolved in approximately 48 g of $H_2O$ (Table 4), and the pH was adjusted to pH=8. Addition of lysine solution to SLS resulted in a clear solution with no sign of precipitate formation.

Figure 6:
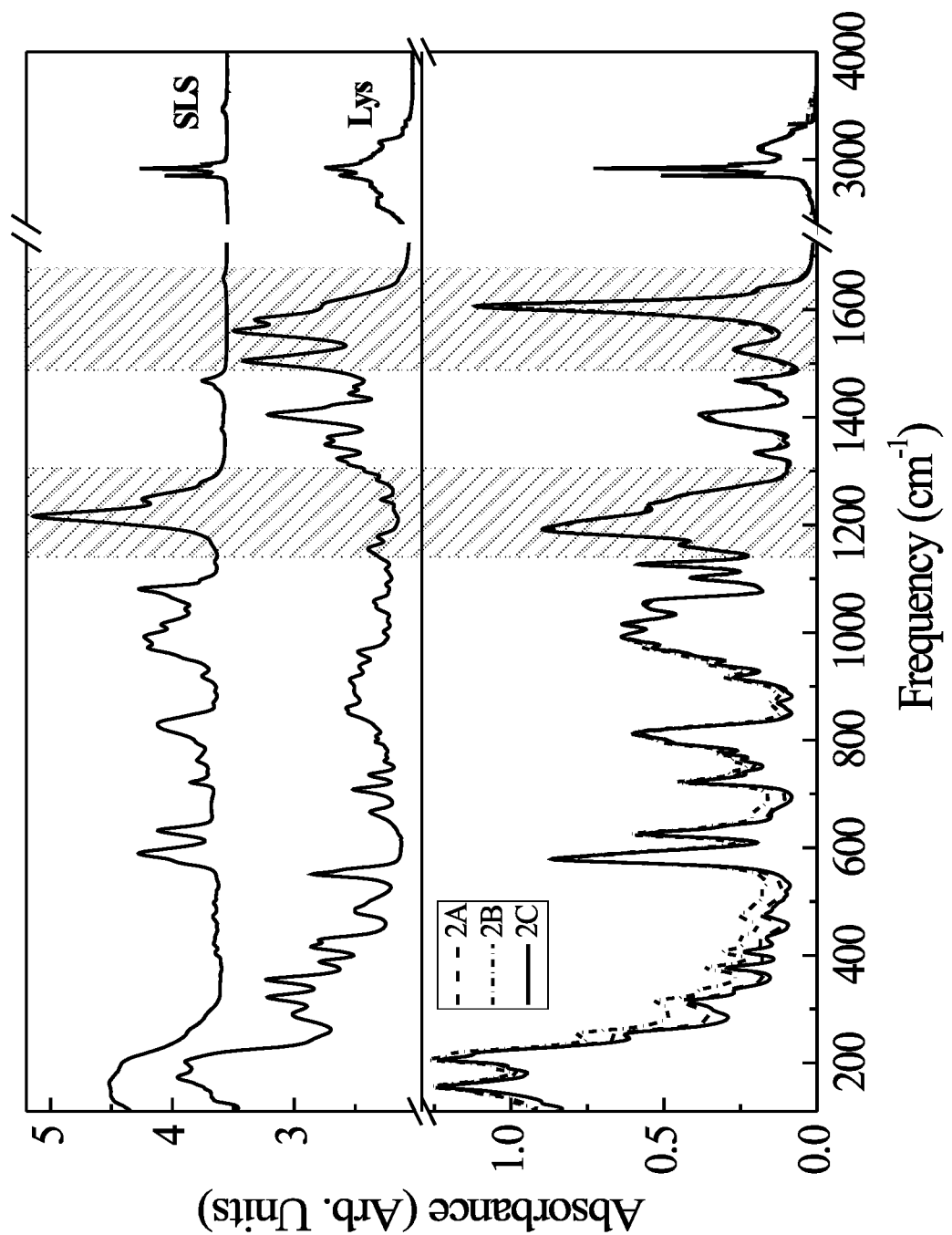
FIG. 6 shows the infrared spectra of samples 2A, 2B and 2C vs. SLS and L-Lysine powders. Shaded regions are examples of SLS and lysine associated bands that can be used for the identification of these components in samples 2A, 2B and 2C, SLS and Lysine spectra are offset for clarity.

To characterize the composition of samples 2A, 2B and 2C, infrared spectroscopic analysis was performed as described in Example 1. FIG. 6 shows the vibrational spectra of samples 2A, 2B and 2C as well the pure arginine and SLS absorption profiles. Clear fingerprints of lysine and SLS are apparent in the spectra of samples 2A, 2B and 2C. For example, the band near 1200 $cm^{-1}$ that corresponds to the $SO_2$ asymmetric vibration ($v_{as}(SO_2)$) is clearly observed in samples 2A, 2B and 2C (Viana et al. (2012), Adv. Phys. Chem., 2012, 1-14). Strong C—H stretching modes ($v_{as}$ (CH)) near 2900 $cm^{-1}$ serve as another distinct indicator of the lauryl sulfate component. A cluster of bands near 1600 $cm^{-1}$ is a unique fingerprint of lysine that arises due to a combination of bending modes of amino groups and stretching vibration of the carboxylate group (Barth (2000), Prog. Biophys. Mol. Biol., 74, 141-173; Hernández et al. (2010), J. Phys. Chem. B 114 (2), 1077-1088). Presence of both components, lysine and LS in the solid phase confirms that the dominant component of Samples 2A, 2B and 2C is not a result of zinc hydroxide and/or zinc lauryl sulfate formation. Importantly, the bands of lysine and lauryl sulfate in samples 2A, 2B and 2C are substantially different in their intensity, shape/width profile and peak positions from those of the pure lysine and SLS materials. This indicates modifications to the local structure of the compounds due to chemical interaction, which cannot be achieved just from a physical mixture of two compounds. The FTIR spectra of samples 2A, 2B and 2C are alike, suggesting their similar local structure and that there is no significant effect of pH or starting materials on the complex formation. A broad background in the low frequency range of sample 2B could be due to additional water/moisture presence in this sample or due to an impurity that contributes to the background. Raman spectra of samples 2A, 2B and 2C were also found to closely resemble each other, in agreement with the infrared data.

To establish the ratio between zinc, arginine and lauryl sulfate as well as to identify the presence of other potential ions in the samples, elemental analysis of Zn, N, S, Na, and Cl was performed following a standard protocol. The results of the analysis are shown in Table 5.

In Table 5, the experimental values in samples 2A, 2B and 2C are compared with the calculated/theoretical values for two possible formulas: (i) $Zn(Lys)_2Cl(LS)$, and (ii) $Zn(Lys)_2(LS)_2$. In samples 2A, 2B and 2C, chlorine is present only in small quantities (likely an impurity) and therefore, Cl/Zn ratios are much less than 1, practically zero in samples 2B and 2C. This indicates that the $Zn(Lys)_2Cl(LS)$ composition can be ruled out for the precipitates. The LS/Lys ratio for all three samples is close to 1, in a better agreement with the $Zn(Lys)_2(LS)_2$ composition. For samples 2A and 2C the Lys/Zn and LS/Zn ratios are also closer to the theoretical composition of $Zn(Lys)_2(LS)_2$, although some excess of zinc is present in sample 2A. Similarly, sample 2B displays an excess amount of zinc relative to Lysine and LS, resulting in substantially lower Lys/Zn and LS/Zn ratios. This suggests that some form of $Zn(OH)_2$ might be also formed at this pH and is present in the precipitate. An alternative composition for instance, Zn(Lys)(LS)(OH) for sample 2B cannot be ruled out based on the elemental analysis, but this is not supported by the FTIR/Raman data where all three samples display similar spectral profiles suggesting similar local structures.

The composition of samples 2A, 2B and 2C was further determined by XPS, which was performed as described in Example 1. Detected elements and their respective atomic percentages for each sample are shown in Table 6. The percentages of the aliphatic ($CH_2$) and carboxylate C ($COO^-$) functional groups are also indicated in Table 6. N was detected in both charged and uncharged chemical states and the percentages of both are shown in Table 6. As shown in Table 7, atomic ratios were also calculated from the compositional data to determine the stoichiometries of the elements detected and compare those with the theoretical values for $Zn(Lys)_2(LS)_2$.

TABLE 5

Summary of elemental analysis for samples 2A, 2B and 2C.

| | | | | | | Molar Ratio | | | |
|---|---|---|---|---|---|---|---|---|---|
| | Zn(%) | N(%) | S(%) | Cl(%) | Na(%) | Lys/Zn | LS/Zn | LS/Lys | Cl/Zn |
| Sample 2A | 9.13 | 6.15 | 7.53 | 0.75 | 0.09 | 1.6 | 1.7 | 1.1 | 0.15 |
| Sample 2B | 12.47 | 5.41 | 7.47 | 0.18 | 0.05 | 1.0 | 1.2 | 1.2 | 0.03 |
| Sample 2C | 8.16 | 6.06 | 7.91 | 0.09 | 0.04 | 1.7 | 2.0 | 1.1 | 0.02 |
| Calc* $Zn(Lys)_2(LS)_2$ | 7.36 | 6.3 | 7.22 | 0 | 0 | 2 | 2 | 1 | 0 |
| Calc** $Zn(Lys)_2Cl(LS)$ | 9.93 | 8.5 | 9.74 | 5.38 | 0 | 2 | 1 | 0.5 | 1 |

*Calculated values for Zn, N, and S, assuming $Zn(Lys)_2(LS)_2$ formula
**Calculated values for Zn, N, S and Cl, assuming $Zn(Lys)_2Cl(LS)$ formula

TABLE 6

Compositions in atomic percent of samples 2A, 2B and 2C determined by XPS.

| Sample | Atomic Percent | | | | | | | | | |
|---|---|---|---|---|---|---|---|---|---|---|
| | $C_{total}$ | $\underline{C}H_2$ | $\underline{C}OO^-$ | O | $N_{total}$ | N | $N^+$ | Zn | S | Na |
| Sample 2A | 69.82 | 51.81 | 3.75 | 18.35 | 6.75 | 3.23 | 3.52 | 1.70 | 3.39 | 0.00 |
| Sample 2B | 68.15 | 51.35 | 3.83 | 19.40 | 6.88 | 3.36 | 3.52 | 2.22 | 3.36 | 0.00 |
| Sample 2C | 69.19 | 52.37 | 3.53 | 18.81 | 6.78 | 3.15 | 3.63 | 1.75 | 3.49 | 0.00 |
| $Zn(Lys)_2(LS)_2$ (Theoretical) | 65.45 | 50.91 | 3.64 | 21.82 | 7.27 | 3.64 | 3.64 | 1.82 | 3.64 | 0.00 |

TABLE 7

Atomic ratios for samples 2A, 2B and 2C determined by XPS.

| Sample | Atomic Ratio | | | | | | | |
|---|---|---|---|---|---|---|---|---|
| | $N_{total}/C_{total}$ | $N^+/N$ | $\underline{C}OO/N_{total}$ | $\underline{C}OO/N^+$ | $N_{total}/S$ | $N^+/S$ | $N_{total}/Zn$ | $S/Zn$ |
| Sample 2A | 0.10 | 1.09 | 0.56 | 1.07 | 1.99 | 1.04 | 3.98 | 2.00 |
| Sample 2B | 0.10 | 1.05 | 0.56 | 1.09 | 2.05 | 1.05 | 3.11 | 1.51 |
| Sample 2C | 0.10 | 1.15 | 0.52 | 0.97 | 1.95 | 1.04 | 3.89 | 2.00 |
| $Zn(Lys)_2(LS)_2$ (Theoretical) | 0.11 | 1.00 | 0.50 | 1.00 | 2.00 | 1.00 | 3.99 | 2.00 |

The compositions of all three samples were similar to the theoretical composition for $Zn(Lys)_2(LS)_2$. The presence of C, O, N and S along with the respective C and N functionalities clearly reflect the presence of Lys and LS in the samples. Zn was also observed in all three samples. However, the Zn concentration for sample 2B was slightly higher than the theoretical value for $Zn(Lys)_2(LS)_2$. As shown in Table 7, the various atomic ratios of organic components for each sample were in good agreement with the theoretical values for $Zn(Lys)_2(LS)_2$. The results indicate that Lys and LS have a 1:1 stoichiometry, as predicted. For samples 2A and 2C, the N/Zn and S/Zn ratios were in excellent agreement with the theoretical values for $Zn(Lys)_2(LS)_2$, and reflect the 2:1 Lys or LS to Zn stoichiometry. For sample 2B, the N/Zn and S/Zn ratios were less than the theoretical values, indicating excess Zn relative to Lys and LS. The fact that both the N/Zn and S/Zn ratios are low may suggest that a minor amount of ZnO or $Zn(OH)_2$ impurity is present in this sample. Overall, the XPS data are consistent with the elemental analysis results and indicate that all three precipitates are composed of $Zn(Lys)_2(LS)_2$, with only sample 2B containing some Zn impurity.

XPS peak position data was further used to determine the chemical bonding environment of elements in the samples. The XPS N, S and Zn peak data for the three samples along with corresponding data for Lys and SLS are shown in Table 8. For all three samples, N is present in the uncharged (N) and positively charged ($N^+$) chemical states. The N and $N^+$ peak positions for samples 2A, 2B and 2C differed from those for solid lysine indicating different N chemical bonding environments. In solid Lys, the alpha C amine is positively charged, while the tail amine is uncharged (Williams et al. (2015), Angew. Chem. Int. Ed., 54 (13), 3973-7). In $Zn(Lys)_2(LS)_2$, the alpha C amine is coordinated to Zn and would not be charged but the tail amine is positively charged and presumably coordinated to LS. These differences in bonding between Lys and $Zn(Lys)_2(LS)_2$ account for the difference in N peak positions between these two materials. In addition, the S peak positions for the three samples differ slightly from that for SLS. This suggests that LS also may be bonded differently in the samples than in SLS and may reflect bonding of the sulfate to the positively charged Lys tail amine. Thus the N and S XPS peak position data for the three samples are consistent with the formation of a new chemical bonding arrangement and support formation of the $Zn(Lys)_2(LS)_2$ complex. Also, the Zn peak positions were similar for all three samples, suggesting Zn is primarily in the same chemical environment for each precipitate. Secondary Zn species were not discernable in the spectra.

TABLE 8

XPS N, S and Zn peak positions for samples 2A, 2B and 2C.

| Sample | XPS Peak, eV | | | |
|---|---|---|---|---|
| | N (1s) | $N^+$ (1s) | S (2p) | Zn (2p3/2) |
| Sample 2A | 399.7 | 401.5 | 168.4 | 1021.8 |
| Sample 2B | 399.6 | 401.5 | 168.4 | 1021.8 |
| Sample 2C | 399.6 | 401.5 | 168.5 | 1021.8 |
| Lysine | 399.0 | 400.9 | — | — |
| SLS | — | — | 168.7 | — |

Figure 7:
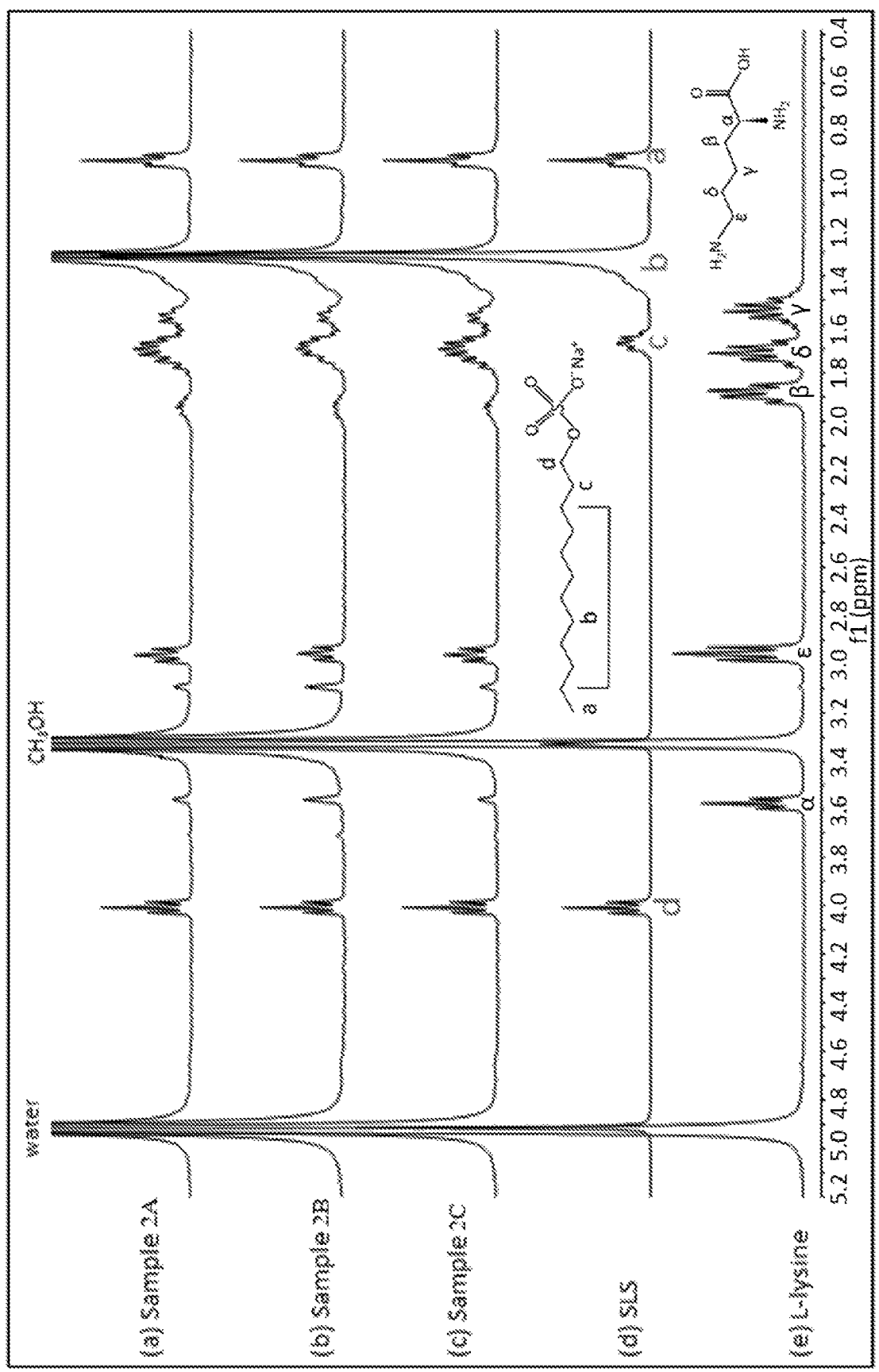
FIG. 7 shows $^1H$ NMR spectra of samples 2A, 2B and 2C, SLS and L-Lysine in d-methanol and their peak assignments.

To further understand the structure of a Zn-Lys-LS complex, $^1$H NMR spectroscopy was applied to the sample 2A, 2B and 2C in methanol. $^1$H NMR spectroscopy was performed as described in Example 1. Because these samples are not completely dissolved in methanol, the supernatant was sampled and analyzed by NMR. As shown in FIG. 7. $^1$H NMR spectra of three samples are identical in methanol and no structural differences are detected. The chemical shifts corresponding to LS in samples 2A, 2B and 2C do not show notable changes, implying that the interaction between LS and Zn, if present, is weak. In contrast, $^1$H chemical shifts corresponding to lysine in the three samples show detectable changes. Particularly, a proton peak in the complex displays a significant line broadening and shifts from 3.55 ppm to 3.8 ppm, likely due to zinc binding. In fact, such exchange line-broadening has been observed in Zn-Lysine complex (ZLC) in water. Moreover, based on the peak integrals in $^1$H NMR spectra shown in FIG. 7, it is concluded that the mole ratio between LS and Lysine in samples 2A, 2B and 2C is 1:1.

$^{13}$C NMR spectroscopy was further performed to analyze the molecular interaction in these samples. $^{13}$C NMR spectra were acquired on a Bruker Avance III HD spectrometer (Bruker-Biospin, Billerica, Mass., USA) with a 5 mm BBI probe operating at 75.4 MHz at 25° C. Consistent with the $^1$H NMR data, the carbonyl carbon of lysine at 174 ppm in sample 2A is significantly broadened due to an exchange effect, supporting lysine interaction with zinc. This result is in good agreement with the $^1$H NMR finding that a proton of lysine in this complex has exchange broadening. However, the chemical shifts corresponding to LS and lysine in sample 2A do not show significant changes in $^{13}$C NMR spectrum. The chemical shift difference may be limited by the solubility of sample in methanol in $^{13}$C NMR spectroscopy.

Figure 8:
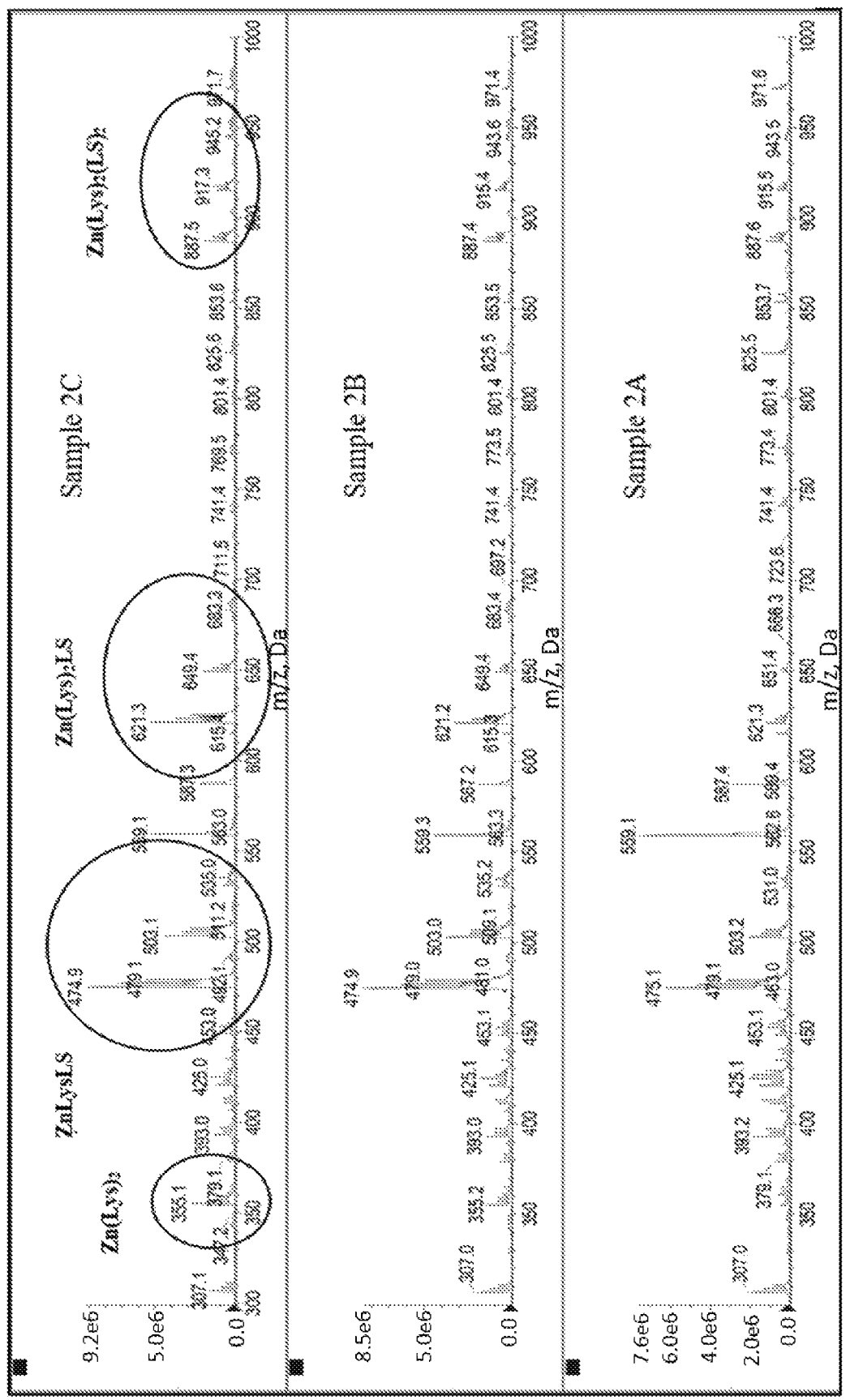
FIG. 8 shows the mass spectrum of samples 2A, 2B and 2C in methanol under a positive detection mode.
Figure 9:
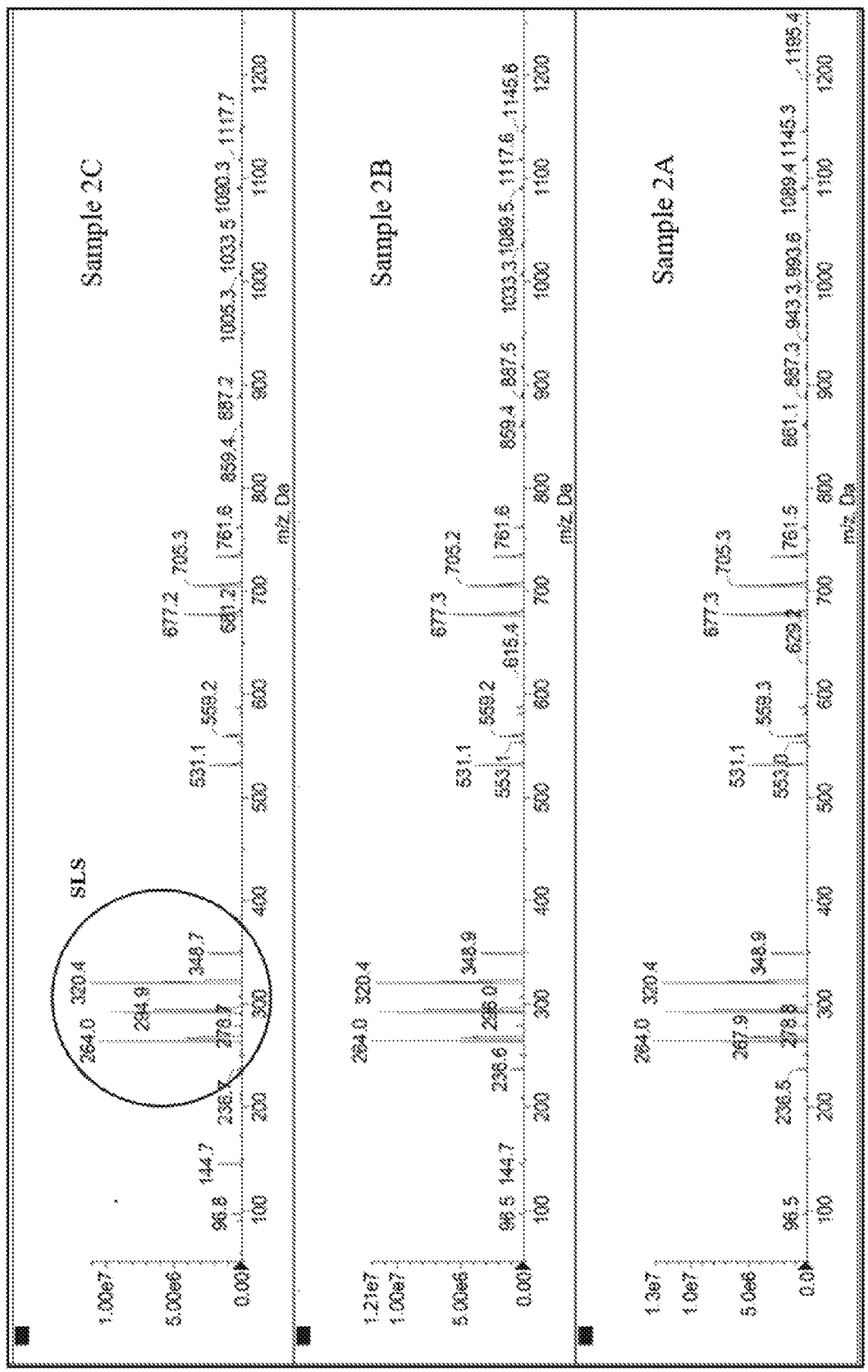
FIG. 9 shows the mass spectrum of samples 2A, 2B and 2C in methanol under a negative detection mode.

To study the $Zn(Lys)_2(LS)_2$ complex structure further, LC-MS analysis was performed on samples 2A, 2B and 2C. LC-MS analysis was carried out as described in Example 1. FIG. 8 and FIG. 9 show the mass spectrometry data for samples 2A, 2B and 2C in methanol under positive and negative detection modes. Because the complexes were not fully soluble in methanol, supernatant was measured in all cases. MS under a positive detection mode revealed several zinc species, including $(Zn(Lys)_2)^{2+}$ (at 355 Da), $(Zn(Lys)LS)^+$ (at 475 Da), $(Zn(Lys)_2LS)$ (at 621 Da), and $Zn(Lys)_2(LS)_2$ (at 887 Da). This result is in agreement with the elemental analysis and spectroscopic data. The spectra of all three samples are found to be similar with the exception that sample 2A does not display $(Zn(Lys)_2)_2^+$ complex, likely due to its low intensity since sample 2A exhibits the lowest MS signal among three samples. All species containing LS appear as a cluster of peaks separated by 28 Dalton due to LS chain distribution ($C_{12}$ to $C_{18}$). Finally, as expected, free LS is identified by MS under a negative detection mode (FIG. 9). The four peaks near 300 Da with mass difference of 28 Dalton correspond to free LS and indicate the LS distribution with $[(CH_2)_2]$ variation from $C_{12}$ to $C_{18}$.

Figure 10A:
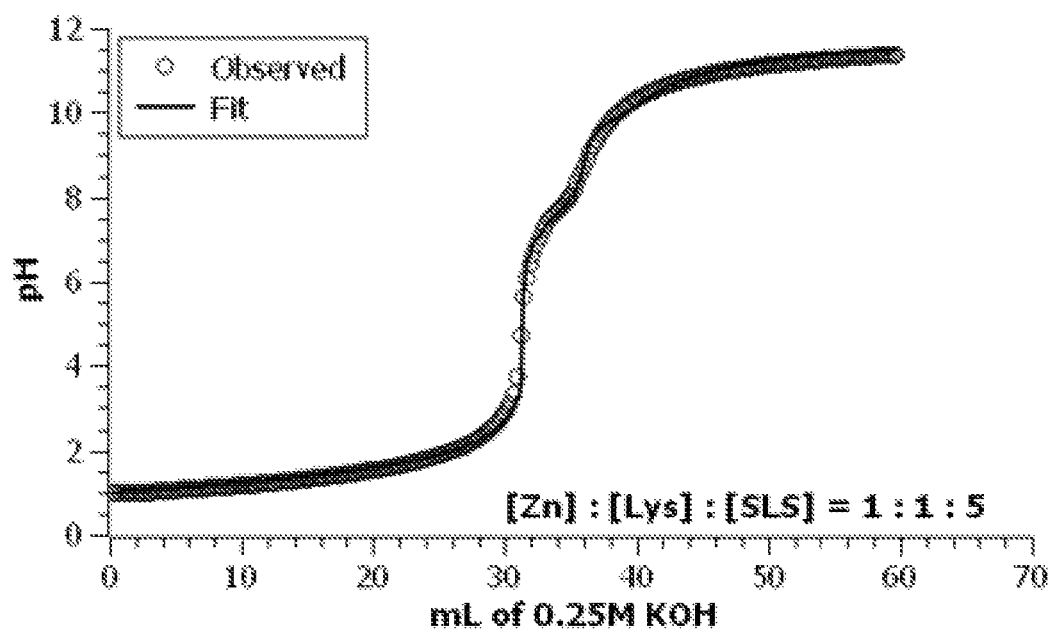
FIGS. 10A, B and C show experimental potentiometric titration curves (circles) and fits (solid lines) for the zinc, lysine, SLS systems ([Zn]: [Lys]: [SLS]=1:1:5 (FIG. 10A), 1:1:10 (FIG. 10B) or 1:1:20 (FIG. 10C)).
Figure 10B:
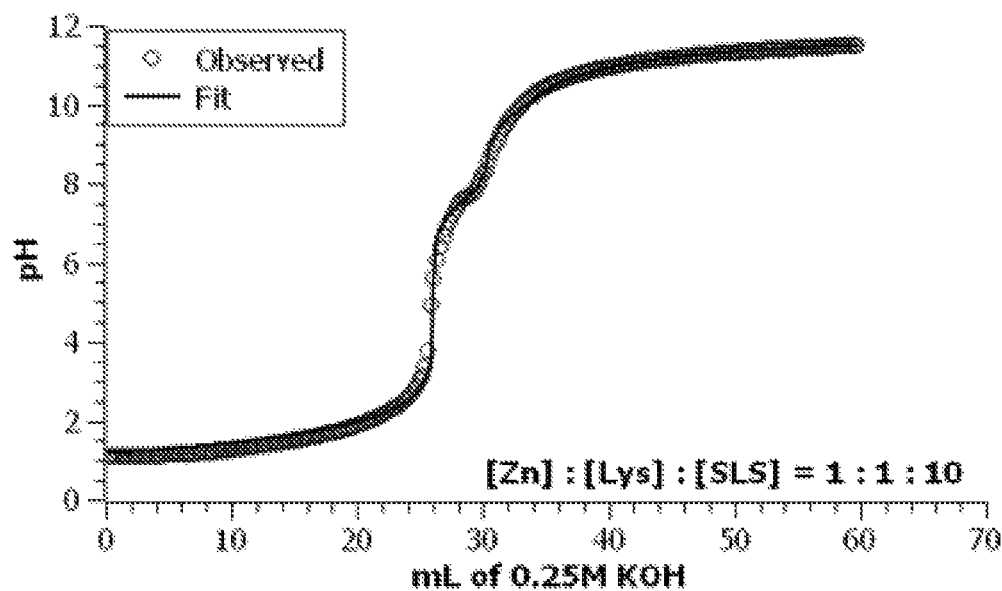
FIG. 10D shows speciation diagram for the zinc, lysine, SLS system at 0.2M ionic strength and pH=8 as a function of SLS concentration.
Figure 10C:
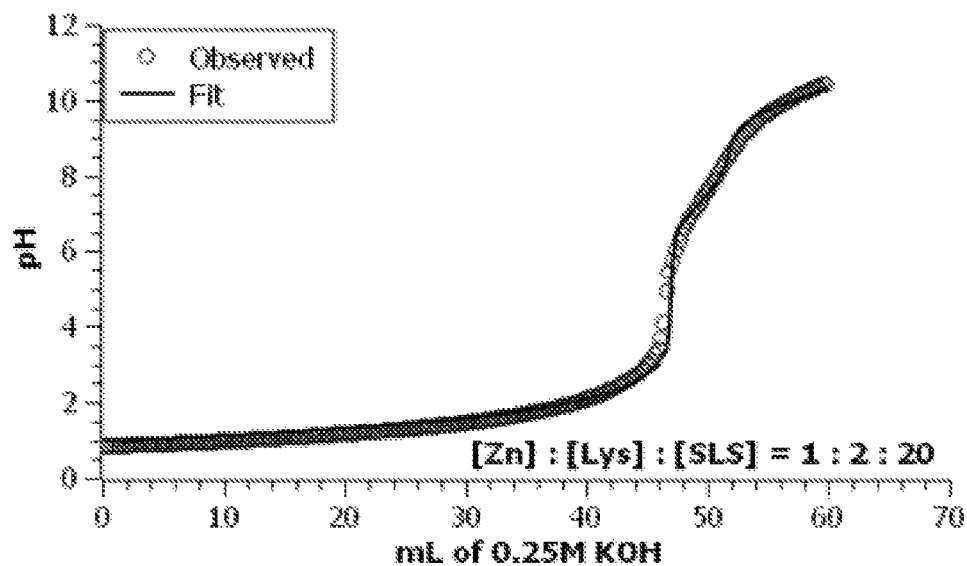

Potentiometric titration is one of the most commonly used techniques to determine metal-ligand binding constants (Martell et al. (1992), Determination and Use of Stability Constants, 2nd ed. Wiley. New York). The technique is based on the principle that hydrogen ion concentration during a pH-titration is sensitive to the protonation state and binding constant of ligands and metals in a given solution. By performing appropriate titration experiments and applying curve-fitting techniques, it is possible to calculate metal-ligand stability constants. A series of titration experiments were performed to determine the binding constants relevant to the zinc/lysine/SLS system. Titration experiments were performed using a Metrohm Titrando 902 auto-titration unit with a pH electrode. A solution of 0.25M KOH was freshly prepared in a 50:50 mixture of glycerin:de-ionized water. Separately, solutions containing $Zn(NO_3)_2.6H_2O$, SLS, $KNO_3$, and Lysine-HCl were prepared in a 50:50 mixture of glycerin:de-ionized water. All solutions were prepared with a concentration of 100 mM $KNO_3$ and 5 mM Zn. The concentrations of Lysine-HCl and SLS were adjusted to achieve various mole ratios of Zn:lysine:SLS. Prior to performing the titration experiments, each solution was adjusted to pH=1.0 using $HNO_3$. Titrations were conducted in a jacketed vessel with temperature maintained at 25 C. With rapid stirring, the 0.25M KOH was added to each test solution at a dosing rate of 0.5 mL/min until a final pH of 12 was achieved. The solution pH was recorded at 10 s intervals. 250 data points were collected for each titration. Titration curves were analyzed using SUPERQUAD to fit the stability constants. The best fit to the experimental data was obtained by including a species formulated as $Zn(HLys)_2(LS)_2$ (FIG. 10A-C). $Zn(HLys)_2(LS)_2$, where lysine side-chain amino group is protonated at studied pH conditions, is the same as $Zn(Lys)_2(LS)_2$ described above. Stability constants determined by potentiometric titration for the Zn, Lysine, SLS system is shown in Table 9.

TABLE 9

Stability constants determined by potentiometric titration for the Zn, Lysine, SLS system.

| Complex | Log(B) | sigma |
|---|---|---|
| HLys | 10.07 | — |
| $H_2Lys$ | 19.21 | — |
| $H_3Lys$ | 21.47 | — |
| HLS | −2.0 | — |
| ZnHLys | 14.68 | — |
| $ZnH_2Lys_2$ | 28.34 | — |
| ZnLS | 1.84 | 0.47 |
| $ZnLS_2$ | 4.29 | 0.63 |
| ZnHLysLS | 16.96 | 0.17 |
| $ZnH_2Lys_2LS_2$ | 32.86 | 0.06 |

Figure 10D:
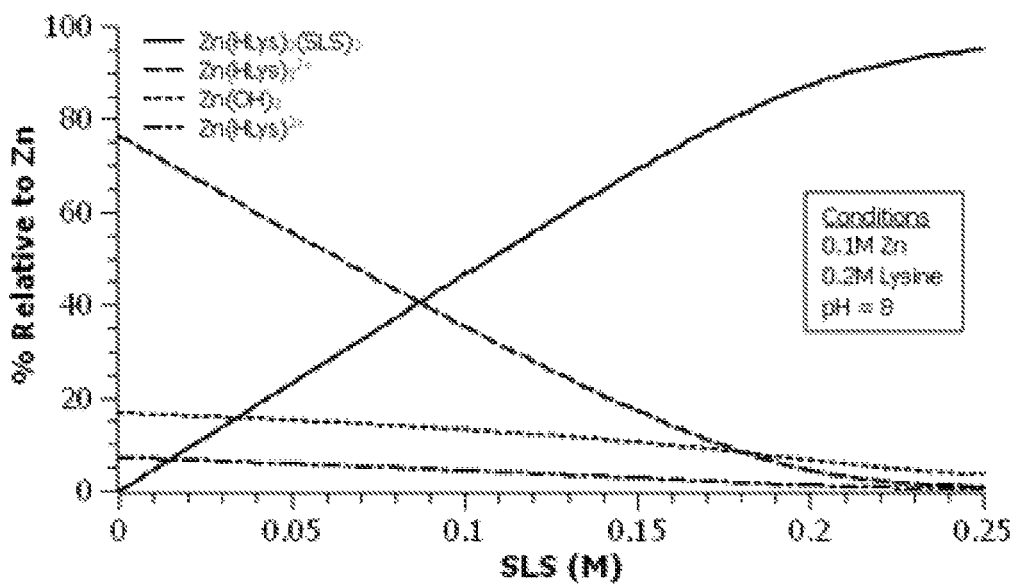

The stability constant for $Zn(HLys)_2(LS)_2$ was determined as log(B)=32.86. The stepwise stability constant for the reaction of $Zn(HLys)_2$ with two equivalents of SLS is log(K)=4.53. The relatively large stability constant for this complex indicates that formation is highly favored. Speciation calculations (FIG. 10D) on a system containing 0.1M Zn, 0.2M lysine, pH=8, and I=0.1M with a varying concentration of SLS indicate that SLS reacts nearly quantitatively with $Zn(HLys)_2$ to form $Zn(HLys)_2(LS)_2$.

The Density Functional Theory (DFT) calculations were performed to check whether the formation of Zn-Lys-LS complex where LS is directly bound to zinc is energetically favorable. DFT calculations were done as described in Example 1. The results are shown below.

| | $\Delta G^0$ (kcal/mol) | $K_{eq}$ |
|---|---|---|
| $[Zn(Lys)_2Cl]^+(aq) + Ls^-(aq) \rightarrow [Zn(Lys)_2Ls]^+(aq) + Cl^-(aq)$ | 13.7 | $9.0 \times 10^{-11}$ |
| $[Zn(Lys)_2Cl]^+(aq) + 2Ls^-(aq) \rightarrow [Zn(Lys)_2Ls_2](aq) + Cl^-(aq)$ | 16.6 | $6.7 \times 10^{-13}$ |
| $[Zn(Lys)_2Cl]^+(aq) + Ls^-(aq) \rightarrow [ZnLysLsCl](aq) + Lys(aq)$ | 14.0 | $5.4 \times 10^{-11}$ |
| $[Zn(Lys)_2Cl]^+(aq) + Ls^-(aq) \rightarrow [ZnLysLs]^+(aq) + Lys(aq) + Cl^-(aq)$ | 20.4 | $1.1 \times 10^{-15}$ |

The computational data demonstrate that each of the reactions above would be unfavorable. LS$^-$ is so bulky that it causes a large steric hindrance and a low coordination number. In the example with two LS ligands, the second LS ion is interacting with the $NH_2$ group on one lysine ligand via hydrogen bonding. In the input structure LS$^-$ was coordinated to Zn directly but shifted during the optimization due to steric hindrance effects, thus favoring 5-coordination over 6-coordination complex. In all four products LS$^-$ acts as a monodentate ligand without forming a chelate ring.

Example 3—Antibacterial Testing

The chelation of zinc can modify its efficacy as an antibacterial agent. To determine the antibacterial activity of zinc-amino acid-lauryl sulfate complexes, experiments were conducted to measure the metabolic inhibition of *S. mutans* after treatment with $Zn(NO_3)_2$, ZLC, $Zn(Lys)_2(LS)_2$ (prepared in Example 2, sample 2C), $[Zn(Arg)_2]^{2+}$, $Zn(Arg)_2(LS)_2$ (prepared in Example 1, sample 1B), and SLS. *S. mutans* is one of the prevalent bacteria present in the oral cavity. A concentrated suspension of *S. mutans* in 135 mM KCl was treated with a known concentration of zinc salt to obtain a final zinc concentration of 2.5 ppm. In the case of SLS, an equimolar amount of SLS was added to match the concentration of LS in the samples of $Zn(Lys)_2(LS)_2$. Using an autotitrator (Methrom Titrando 902) equipped with a 0.01M solution of KOH, the bacterial suspension was equilibrated to pH=7. After equilibrating, glucose was added to the solution. The autotitrator maintained the pH at 7 through the precise addition of KOH solution. The experiment was allowed to proceed for 30 minutes and the volume of base added was recorded at 10 second intervals. After 30 mins, a growth curve of base addition over time was obtained. The area under this curve was compared to the area under the curve for a control sample containing only bacteria and used to calculate a % reduction value. The control sample was analyzed from the same bacterial suspension as the test sample and the two samples were analyzed within 3 hours of each other. In order for data from a given suspension of *S. mutans* to be included, the control sample must consume at least 5 mL of base solution during the 30 minute time period. The % reduction for each sample is shown in Table 10.

TABLE 10

Reduction in the metabolic activity of *S. mutans* after treatment with various compounds.

| Sample | % Metabolic Reduction |
| --- | --- |
| $Zn(NO_3)_2$ | 67.16 ± 2.49 |
| Sodium lauryl sulfate | 34.12 ± 1.56 |
| ZLC | 53.90 ± 2.36 |
| $Zn(Lys)_2(LS)_2$ | 67.19 ± 3.97 |
| $[Zn(Arg)_2]^{2+}$ | 67.19 ± 0.32 |
| $Zn(Arg)_2(LS)_2$ | 72.53 ± 3.76 |

The antibacterial testing results show that despite low solubility, $Zn(Lys)_2(LS)_2$ shows a better antibacterial performance compared to ZLC. Similarly $Zn(Arg)_2(LS)_2$ shows a directionally improved antibacterial performance compared to $[Zn(Arg)_2]^{2+}$.

While the disclosure has been described with respect to specific examples including presently preferred modes of carrying out the disclosure, those skilled in the art will appreciate that there are numerous variations and permutations of the above described systems and techniques. It is to be understood that other embodiments may be utilized and structural and functional modifications may be made without departing from the scope of the present disclosure. Thus, the scope of the disclosure should be construed broadly as set forth in the appended claims.

The invention claimed is:

1. A zinc-amino acid-lauryl sulfate complex, wherein the complex is in powder form.

2. The complex of claim 1, wherein the zinc-amino acid-lauryl sulfate has the chemical structure [Zn(amino acid)$_2$](LS)$_2$.

3. The complex of claim 1, wherein the complex is water insoluble.

4. The complex of claim 1, wherein the amino acid is a basic amino acid.

5. The complex of claim 4, wherein the basic amino acid is arginine or lysine.

6. The complex of claim 5, wherein the basic amino acid is arginine and the complex has the chemical structure [Zn(Arg)$_2$](LS)$_2$.

7. The complex of claim 5, wherein the basic amino acid is lysine and the complex has the chemical structure [Zn(Lys)$_2$](LS)$_2$.

8. An oral care composition comprising the zinc-amino acid-lauryl sulfate complex according to claim 1, wherein the zinc-amino acid-lauryl sulfate complex is added to the composition as a preformed complex.

9. The oral care composition of claim 8, wherein the zinc-amino acid-lauryl sulfate complex is present in an amount of 0.1 to 10% by weight of the composition.

10. The oral care composition of claim 8, wherein the oral care composition is a dentifrice.

11. The oral care composition of claim 8, wherein the oral care composition comprises a fluoride ion source.

12. A method of producing the zinc-amino acid-lauryl sulfate complex according to claim 1, comprising combining sodium lauryl sulfate and a zinc-amino acid complex in an aqueous solution.

13. The method of claim 12, wherein the zinc-amino acid-lauryl sulfate complex is a zinc-basic amino acid-lauryl sulfate complex.

14. The method of claim 13, wherein the zinc-amino acid complex is [Zn(Lys)$_2$Cl]$^+$Cl$^-$ (ZLC) or [Zn(Arg)$_2$Cl]$^+$Cl$^-$.

15. The method of claim 13, wherein the zinc-amino acid complex is prepared by combining a soluble zinc salt and a basic amino acid, e.g., arginine or lysine, in an aqueous solution.

16. The method of claim 12, wherein the method further comprises a step of filtering and drying the zinc-amino acid-lauryl sulfate complex.

* * * * *